United States Patent
Pan et al.

(10) Patent No.: US 12,226,441 B2
(45) Date of Patent: Feb. 18, 2025

(54) COMPOSITION FOR INHIBITING INTESTINAL PERMEABILITY, TREATING LEAKY GUT RELATED DISEASES AND/OR PREVENTING LEAKY GUT RELATED DISEASES

(71) Applicant: INDUSTRIAL TECHNOLOGY RESEARCH INSTITUTE, Hsinchu (TW)

(72) Inventors: I-Hong Pan, Zhubei (TW);
Kuei-Chang Li, Taipei (TW);
Zong-Keng Kuo, Hsinchu (TW);
Chu-Hsun Lu, Kaohsiung (TW);
Yen-Wu Hsieh, Zhudong Township (TW); Shu-Fang Wen, Baoshan Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 18/327,583

(22) Filed: Jun. 1, 2023

(65) Prior Publication Data

US 2024/0165181 A1 May 23, 2024

Related U.S. Application Data

(62) Division of application No. 17/138,610, filed on Dec. 30, 2020, now Pat. No. 11,701,399.

(60) Provisional application No. 62/981,720, filed on Feb. 26, 2020.

(30) Foreign Application Priority Data

Dec. 25, 2020 (TW) ................. 109146258

(51) Int. Cl.
| | |
|---|---|
| *A61K 36/074* | (2006.01) |
| *A61K 31/575* | (2006.01) |
| *A61K 36/185* | (2006.01) |
| *A61K 36/725* | (2006.01) |
| *A61K 36/77* | (2006.01) |
| *A61P 1/00* | (2006.01) |
| *A61P 25/20* | (2006.01) |
| *A61P 25/28* | (2006.01) |

(52) U.S. Cl.
CPC .......... *A61K 36/074* (2013.01); *A61K 31/575* (2013.01); *A61K 36/185* (2013.01); *A61K 36/725* (2013.01); *A61K 36/77* (2013.01); *A61P 1/00* (2018.01); *A61P 25/20* (2018.01); *A61P 25/28* (2018.01)

(58) Field of Classification Search
None
See application file for complete search history.

(56) References Cited

U.S. PATENT DOCUMENTS

| | | |
|---|---|---|
| 6,110,891 A | 8/2000 | Pusztai et al. |
| 7,799,763 B2 | 9/2010 | Okada et al. |
| 7,947,283 B2 | 5/2011 | Tu et al. |
| 10,398,671 B2 | 9/2019 | Morris |
| 2011/0065629 A1 | 3/2011 | Fujikawa |
| 2014/0147484 A1 | 5/2014 | Wu et al. |
| 2015/0296851 A1 | 10/2015 | Zhao |
| 2019/0303538 A1* | 10/2019 | Hsieh ................. C07J 9/005 |

FOREIGN PATENT DOCUMENTS

| | | | |
|---|---|---|---|
| CN | 1543815 A | | 11/2004 |
| CN | 101205517 A | * | 6/2008 |
| CN | 103621993 A | | 3/2014 |
| CN | 103478563 B | | 11/2014 |
| CN | 104758578 A | | 7/2015 |
| CN | 105412157 A | | 3/2016 |
| CN | 105412237 A | | 3/2016 |
| CN | 105983055 A | | 10/2016 |
| CN | 106722985 A | | 5/2017 |
| CN | 109275856 A | * | 1/2019 |
| CN | 104873745 B | | 2/2019 |
| CN | 109717342 A | | 5/2019 |
| CN | 110354200 A | | 10/2019 |
| CN | 111184176 A | | 5/2020 |
| EP | 2 987 495 A1 | | 2/2016 |
| KR | 2003-0012359 A | | 2/2003 |
| TW | 201916876 A | | 5/2019 |
| WO | WO 2019/034396 A1 | | 2/2019 |

OTHER PUBLICATIONS

Fang, "Poor Sleep in Old Age, The Traditional Way to Deal With It", Modern Health, Oct. 2017, pp. 48-49 with an English translation.
Taiwanese Office Action and Search Report dated Sep. 18, 2023 for Application No. 112108253.
Wenquan, "Who Stole Your Sleep", Food and Life, Sep. 2015, pp. 60-61 with an English translation.
"Black and White Fungus, Reishi Mushroom, Longan Sweet Soup with Jujubes and Lotus Seeds," dated Oct. 8, 2019, with English translation (1 page total).
Aguas et al., "Prevalence of irritable bowel syndrome (IBS) in first-degree relatives of patients with inflammatory bowel disease (IBD)," Journal of Crohn's and Colitis, vol. 5, 2011, pp. 227-233.

(Continued)

*Primary Examiner* — Susan Hoffman
(74) *Attorney, Agent, or Firm* — Birch, Stewart, Kolasch & Birch, LLP

(57) ABSTRACT

A composition for inhibiting intestinal permeability, treating leaky gut related diseases and/or preventing leaky gut related diseases including a Chinese herbal compound material or a Chinese herbal compound extract is provided. The Chinese herbal compound material includes *Ganoderma*, red jujube, longan and lotus seed. Moreover, the Chinese herbal compound extract includes a *Ganoderma* extract, a red jujube extract, a longan extract and a lotus seed extract.

14 Claims, 28 Drawing Sheets

Specification includes a Sequence Listing.

(56) References Cited

OTHER PUBLICATIONS

Amar et al., "Blood microbiota dysbiosis is associated with the onset of cardiovascular events in a large general population: the D.E.S.I.R. study," PLoS One, vol. 8, Issue 1, Jan. 25, 2013, pp. 1-8.
Ammori et al., "Early increase in intestinal permeability in patients with severe acute pancreatitis: correlation with endotoxemia, organ failure, and mortality." Journal of Gastrointestinal Surgery, vol. 3, No. 3, 1999, pp. 252-262.
Anderson et al., "Physiology and function of the tight junction," Cold Spring Harbor Perspectives in Biology, 2009, pp. 1-16.
Arrieta et al., "Alterations in intestinal permeability," Gut, vol. 55, 2006, pp. 1512-1520.
Bai et al., "Carbohydrate Polymers, Longan pulp polysaccharides relieve intestinal injury in vivo and in vitro by promoting tight junction expression," vol. 229, 115475, 2019, 12 pages.
Bosi et al., "Increased intestinal permeability precedes clinical onset of type 1 diabetes," Diabetologia, vol. 49, 2006 (published online Oct. 7, 2006), pp. 2824-2827.
Buhner et al., "Genetic basis for increased intestinal permeability in families with Crohn's disease: role of CARD15 3020insC mutation?," Gut, vol. 55, 2006 (published online Jul. 29, 2005), pp. 342-347.
Camilleri et al., "Irritable bowel syndrome: methods, mechanisms, and pathophysiology. The confluence of increased permeability, inflammation, and pain in irritable bowel syndrome," Am J Physiol Gastrointest Liver Physiol, vol. 303, Jul. 26, 2012, pp. G775-G785.
Camilleri, "Leaky gut: mechanisms, measurement and clinical implications in humans," Gut, vol. 68, 2019 (published online May 10, 2019), pp. 1516-1526.
Cani et al., "Involvement of gut microbiota in the development of low-grade inflammation and type 2 diabetes associated with obesity," Gut Microbes, vol. 3, Issue 4, 2012, pp. 279-288.
Chelakkot et al., "Mechanisms regulating intestinal barrier integrity and its pathological implications," Experimental & Molecular Medicine, vol. 50, No. 103, 2018, pp. 1-9.
D'Incà et al., "Intestinal permeability test as a predictor of clinical course in Crohn's disease," The American Journal of Gastroenterology, vol. 94, No. 10, Oct. 1999, pp. 2956-2960.
Davies et al., "Intestinal permeability and orocaecal transit time in elderly patients with Parkinson's disease," Postgrad Med J, vol. 72, 1996, pp. 164-167.
De Magistris et al., "Alterations of the intestinal barrier in patients with autism spectrum disorders and in their first-degree relatives," J Pediatr Gastroenterol Nutr, vol. 51, No. 4, Oct. 2010, pp. 418-424.
Doig et al., "Increased intestinal permeability is associated with the development of multiple organ dysfunction syndrome in critically ill ICU patients," American Journal of Respiratory and Critical Care Medicine, vol. 158, 1998, pp. 444-451.
Ely, "Is psoriasis a bowel disease? Successful treatment with bile acids and bioflavonoids suggests it is," Clinics in Dermatology, vol. 36, 2018, pp. 376-389.
English abstract of Deitch et al., "Effect of hemorrhagic shock on bacterial translocation, intestinal morphology, and intestinal permeability in conventional and antibiotic-decontaminated rats," Crit Care Med, vol. 18, No. 5, 1990, pp. 529-536.
Fang et al., "Evaluation of the microbial diversity in amyotrophic lateral sclerosis using high-throughput sequencing," Frontiers in Microbiology, vol. 7, Article 1479, Sep. 20, 2016, pp. 1-7.
Farhadi et al., "Susceptibility to gut leakiness: a possible mechanism for endotoxaemia in non-alcoholic steatohepatitis," Liver International, 2008, pp. 1026-1033.
Forsyth et al., "Increased intestinal permeability correlates with sigmoid mucosa alpha-synuclein staining and endotoxin exposure markers in early Parkinson's disease," PLoS One, vol. 6, Issue 12, Dec. 1, 2011, pp. 1-10.
Goebel et al., "Altered intestinal permeability in patients with primary fibromyalgia and in patients with complex regional pain syndrome," Rheumatology, vol. 47, Jun. 7, 2008, pp. 1223-1227.
Hanaoka et al., "The Water-Soluble Extract from Cultured Medium of *Ganoderma lucidum* (Reishi) Mycelia (Designated as MAK) Ameliorates Murine Colitis Induced by Trinitrobenzene Sulphonic Acid." Scandinavian Journal of Immunology, vol. 74, 2011, pp. 454-462.
Hasnat et al., "Anti-inflammatory activity on mice of extract of Ganoderma lucidum grown on rice via modulation of MAPK and NF-kB pathways," Phytochemistry, 2014, pp. 1-12.
Hijazi et al., "Intestinal permeability is increased in bronchial asthma," Arch Dis Child, vol. 89, 2004, pp. 227-229.
Hollander et al., "Increased intestinal permeability in Crohn's patients and their relatives: an etiological factor," Ann Intern Med, vol. 105, No. 6, Dec. 1986, pp. 883-885.
Hsu et al., "Reishi protein LZ-8 induces FOXP3+treg expansion via a CD45-dependent signaling pathway and alleviates acute intestinal inflammation in mice. Evidence-based Complement," Evidence-Based Complementary and Alternative Medicine, 2013, pp. 1-11.
International Search Report and Written Opinion of the International Searching Authority for International Application No. PCT/GB2021/050505, dated Jun. 1, 2021.
Jackson et al., "Intestinal permeability in patients with eczema and food allergy," The Lancet, Jun. 13, 1981, pp. 1285-1286.
Japanese Office Action for Japanese Application No. 2020-217216, dated Mar. 23, 2022.
Jin et al., "Effects of polysaccharide from mycelia of Ganoderma lucidum on intestinal barrier functions of rats," International Journal of Biological Macromolecules, vol. 94, 2017, pp. 1-9.
Keating et al., "Intestinal absorptive capacity, intestinal permeability and jejunal histology in HIV and their relation to diarrhoea," Gut, vol. 37, 1995, pp. 623-629.
Keshavarzian et al., "Leaky gut in alcoholic cirrhosis: a possible mechanism for alcohol-induced liver damage," The American Journal of Gastroenterology, vol. 94, No. 1, Jan. 1999, pp. 200-207.
Khan et al., "Mushroom polysaccharides and jiaogulan saponins exert cancer preventive effects by shaping the gut microbiota and microenvironment in ApcMin/+ mice," Pharmacological Research, vol. 148, 2019, pp. 1-11.
Leblhuber et al., "Elevated fecal calprotectin in patients with Alzheimer's dementia indicates leaky gut," J Neural Transm, Feb. 14, 2015, 4 pages total.
Li, "The Magical Uses of Chinese Medicine Secret Recipes at Home", China Medical Science and Technology (1993) p. 67.
Liu et al., "Gut microbiota as a subjective measurement for auxiliary diagnosis of insomnia disorder," Frontiers in Microbiology, vol. 10, Article 1770, Aug. 13, 2019, pp. 1-12.
Liu et al., "Lotus leaf (*Nelumbo nucifer*) and its active constituents prevent inflammatory responses in macrophages via JNK/NF-kB signaling pathway," The American Journal of Chinese Medicine, vol. 42, No. 4, 2014, pp. 869-889.
Liu, "The microbiome as a novel paradigm in studying stress and mental health," Am Psychol, vol. 72, No. 7, Oct. 2017, pp. 655-667.
Martínez-González et al., "Intestinal permeability in patients with ankylosing spondylitis and their healthy relatives," British Journal of Rheumatology, vol. 33, No. 7, 1994, pp. 644-647.
Morris et al., "Increased intestinal permeability in ankylosing spondylitis—primary lesion or drug effect?" Gut, vol. 32, 1991, pp. 1470-1472.
Nagai et al., "Polysaccharides derived from *Ganoderma lucidum* fungus mycelia ameliorate indomethacin-induced small intestinal injury via induction of GM-CSF from macriohages," Cellular Immunology, vol. 320, 2017, pp. 20-28.
Natividad et al., "Modulation of intestinal barrier by intestinal microbiota: pathological and therapeutic implications," Pharmacological Research, vol. 69, 2013, pp. 42-51.
Nguyen et al., "Overview and systematic review of studies of microbiome in schizophrenia and bipolar disorder," J Psychiatr Res, vol. 99. Apr. 2018, pp. 50-61.
Office Action issued Aug. 16, 2022, in Chinese Patent Application No. 202180003348.4.
Peters et al., "Autoimmune diabetes mellitus and the leaky gut," Proc Natl Acad Sci, vol. 116, No. 30, Jul. 23, 2019, pp. 14788-14790.
Peterson et al., "Intestinal epithelial cells: regulators of barrier function and immune homeostasis," Nature Reviews Immunology, vol. 14, Mar. 2014, pp. 141-153.

(56) References Cited

OTHER PUBLICATIONS

Pike et al., "Increased intestinal permeability in atopic eczema," The Journal of Investigative Dermatology, vol. 86, No. 2, Feb. 1986, pp. 101-104.
Poroyko et al., "Chronic sleep disruption alters gut microbiota, induces systemic and adipose tissue inflammation and insulin resistance in mice," Scientific Reports, Oct. 14, 2016, 11 pages total.
Qin et al., "A metagenome-wide association study of gut microbiota in type 2 diabetes," Nature, vol. 490, Oct. 4, 2012, pp. 55-60.
Raybould, "Gut microbiota, epithelial function and derangements in obesity," The Journal of Physiology, vol. 590, No. 3, 2012 (published online Dec. 19, 2011), pp. 441-446.
Rowin et al., "Gut inflammation and dysbiosis in human motor neuron disease," Physiological Reports, vol. 5, Issue 18, 2017, pp. 1-6.
Salat-Foix et al., "Increased intestinal permeability and Parkinson disease patients: chicken or egg?" The Canadian Journal of Neurological Sciences, vol. 39, 2012, pp. 185-188.
Sharpstone et al., "Small intestinal transit, absorption, and permeability in patients with AIDS with and without diarrhoea," Gut, vol. 45, 1999, pp. 70-76.
Smecuol et al., "Gastrointestinal permeability in celiac disease," Gastroenterology, vol. 112, No. 4, Apr. 1997, pp. 1129-1136.
Stevens et al., "Increased human intestinal barrier permeability plasma biomarkers zonulin and FABP2 correlated with plasma LPS and altered gut microbiome in anxiety or depression," Gut, Aug. 2018, p. 1-5.
Taiwanese Office Action and Search Report for Taiwanese Application No. 109146258, dated Jan. 26, 2022.
Taiwanese Office Action and Search Report for Taiwanese Application No. 109146258, dated Jul. 8, 2021.
Terano et al., "Cell culture of rat gastric fundic mucosa," Gastroenterology, vol. 83, No. 6, Dec. 1982, pp. 1280-1291.
Van Elburg et al., "Intestinal permeability in patients with coeliac disease and relatives of patients with coeliac disease," Gut, vol. 34, 1993, pp. 354-357.
Vaziri et al., "Chronic kidney disease causes disruption of gastric and small intestinal epithelial tight junction," American Journal of Nephrology, vol. 38, 2013 (published online Jul. 23, 2013), pp. 99-103.
Vaziri et al., "Disintegration of colonic epithelial tight junction in uremia: a likely cause of CKD-associated inflammation," Nephrol Dial Transplant, vol. 27, 2012, pp. 2686-2693.
Vazquez-Roque et al., "A Controlled Trial of Gluten-Free Diet in Irritable Bowel Syndrome-Diarrhea Effects on Bowel Frequency and Intestinal Functions," Gastroenterology, vol. 144, No. 5, May 2013, pp. 903-911.
Wei et al., "Suppression of Th17 cell response in the alleviation of dextran sulfate sodium-induced colitis by Ganoderma lucidum polysaccharides," Journal of Immunology Research, May 20, 2018, pp. 1-10.
Wigg et al., "The role of small intestinal bacterial overgrowth, intestinal permeability, endotoxaemia, and tumour necrosis factor alpha in the pathogenesis of non-alcoholic steatohepatitis," Gut, vol. 48, 2001, 206-211.
Wu et al., "Gluten-induced symptoms in diarrhea-predominant irritable bowel syndrome are associated with increased myosin light chain kinase activity and claudin-15 expression," Lab Invest, vol. 97, No. 1, Jan. 2017, pp. 14-23.
Xie et al., "Ganoderma lucidum polysaccharide improves rat DSS-induces colitis by altering cecal microbiota and gene expression of colonic epithelial cells," Food & Nutrition Research, vol. 63, Feb. 12, 2019, pp. 1-12.
Xu-Cong et al., "Polysaccharide peptides from Ganoderma lucidum ameliorate lipid metabolic disorders and gut microbiota dysbiosis in high-fat diet-fed rats," Journal of Functional Foods, vol. 57, 2019, pp. 48-58.
Yacyshyn et al., "Multiple sclerosis patients have peripheral blood CD45RO+ B cells and increased intestinal permeability," Digestive Diseases and Sciences, vol. 41, No. 12, Dec. 1996, pp. 2493-2498.
Yu et al., "Bioactive components in the fruits of Ziziphus jujuba Mill. Against the inflammatory irritant action of Euphorbia plants," Phytomedicine, vol. 19, 2012, pp. 239-244.
Yue et al., "Wild jujube polysaccharides protect against experimental inflammatory bowel disease by enabling enhanced intestinal barrier function," Food & Function, 2015, 10 pages total.

\* cited by examiner

NC: Negative control
Sample 1: Ganoderma extract
Sample 2: Red jujube extract
Sample 3: Longan extract
Sample 4: Lotus seed extract
Sample 6: Mixture extract of Ganoderma and longan
(Weight ratio of the respective herbal raw materials for obtaining the respective extracts is 1:1)
Sample 9: Mixture extract of red jujube and lotus seed
(Weight ratio of the respective herbal raw materials for obtaining the respective extracts is 1:1)
Sample 11: Mixture extract of Ganoderma, red jujube and longan
(Weight ratio of the respective herbal raw materials for obtaining the respective extracts is 1:1:1)
Sample 12: Mixture extract of Ganoderma, red jujube and lotus seed
(Weight ratio of the respective herbal raw materials for obtaining the respective extracts is 1:1:1)
Sample 15A: Mixture extract of Ganoderma, red jujube, longan and lotus seed (Weight ratio of the respective herbal raw materials for obtaining the respective extracts is 1:1:1:1)
PC: Positive control

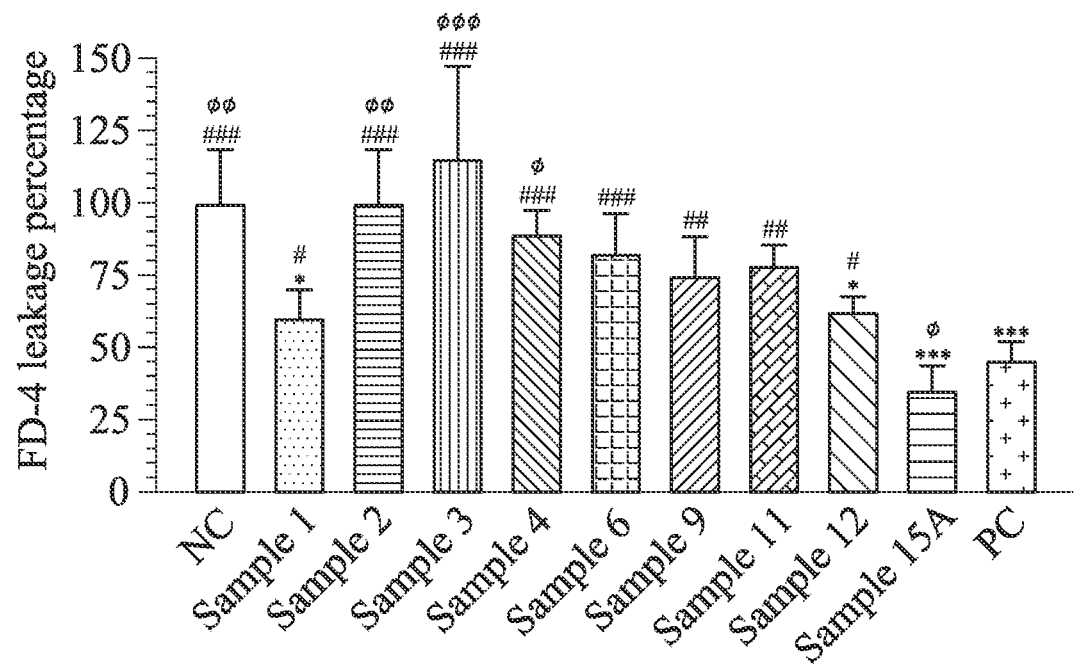

FIG. 3

NC: Negative control
Sample 1: Ganoderma extract
Sample 15N: Mixture extract of Ganoderma, red jujube, longan and lotus seed (Weight ratio of the respective herbal raw materials for obtaining the respective extracts is 1:1:1:0.5)
Sample 15A: Mixture extract of Ganoderma, red jujube, longan and lotus seed (Weight ratio of the respective herbal raw materials for obtaining the respective extracts is 1:1:1:1)
Sample 15O: Mixture extract of Ganoderma, red jujube, longan and lotus seed (Weight ratio of the respective herbal raw materials for obtaining the respective extracts is 1:1:1:3)
Sample 15P: Mixture extract of Ganoderma, red jujube, longan and lotus seed (Weight ratio of the respective herbal raw materials for obtaining the respective extracts is 1:1:1:6)
Sample 15Q: Mixture extract of Ganoderma, red jujube, longan and lotus seed (Weight ratio of the respective herbal raw materials for obtaining the respective extracts is 1:1:1:10)
PC: Positive control

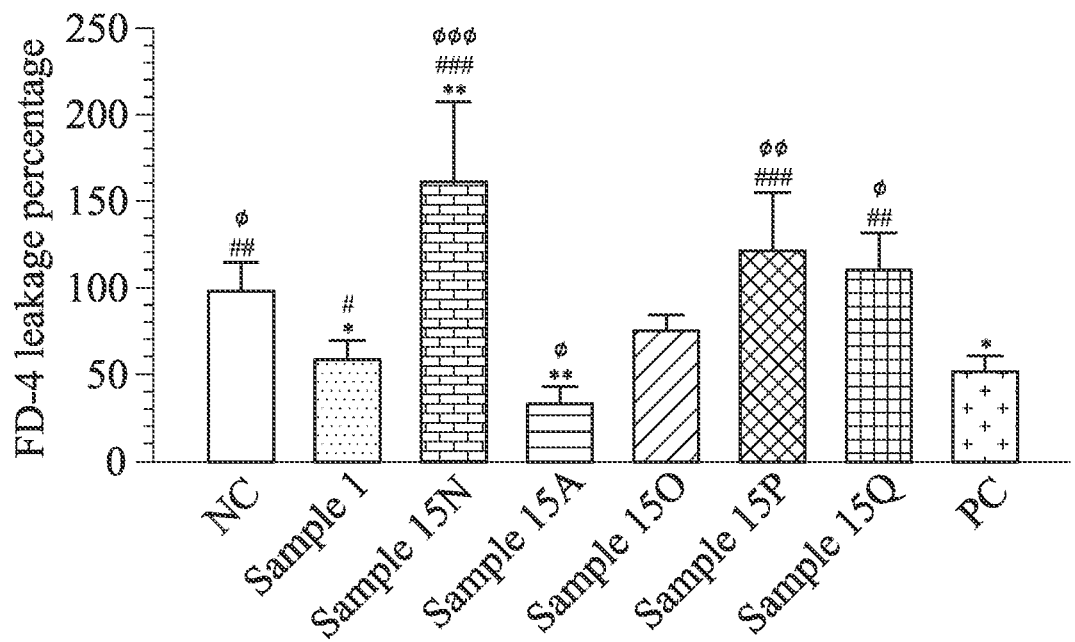

FIG. 4D

NC: Negative control
Sample 15B: Mixture extract of Ganoderma, red jujube, longan and lotus seed
(Weight ratio of the respective herbal raw materials for obtaining the respective extracts is 3:1:1:1)
PC: Positive control NC: Negative control
Sample 15B: Mixture extract of Ganoderma, red jujube, longan and lotus seed
(Weight ratio of the respective herbal raw materials for obtaining the respective extracts is 3:1:1:1)
PC: Positive control NC: Negative control
Sample 15B: Mixture extract of Ganoderma, red jujube, longan and lotus seed
(Weight ratio of the respective herbal raw materials for obtaining the respective extracts is 3:1:1:1)
PC: Positive control

SEQUENCE LISTING

```
Sequence total quantity: 8
SEQ ID NO: 1            moltype = DNA  length = 17
FEATURE                 Location/Qualifiers
misc_feature            1..17
                        note = Forword primer for CLDN3 gene
source                  1..17
                        mol_type = other DNA
                        organism = synthetic construct
SEQUENCE: 1
atcgtgtgct gcgcgtt                                                  17

SEQ ID NO: 2            moltype = DNA  length = 19
FEATURE                 Location/Qualifiers
```

```
misc_feature         1..19
                     note = Reverse primer for CLDN3 gene
source               1..19
                     mol_type = other DNA
                     organism = synthetic construct
SEQUENCE: 2
ggccctccca gatgttctg                                              19

SEQ ID NO: 3         moltype = DNA   length = 23
FEATURE              Location/Qualifiers
misc_feature         1..23
                     note = Forward primer for OCLN gene
source               1..23
                     mol_type = other DNA
                     organism = synthetic construct
SEQUENCE: 3
gtccaatatt ttgtgggaca agg                                         23

SEQ ID NO: 4         moltype = DNA   length = 18
FEATURE              Location/Qualifiers
misc_feature         1..18
                     note = Reverse primer for OCLN gene
source               1..18
                     mol_type = other DNA
                     organism = synthetic construct
SEQUENCE: 4
ggcacgtcct gtgtgcct                                               18

SEQ ID NO: 5         moltype = DNA   length = 23
FEATURE              Location/Qualifiers
misc_feature         1..23
                     note = Forward primer for TJP1 gene
source               1..23
                     mol_type = other DNA
                     organism = synthetic construct
SEQUENCE: 5
agaaggatgt ttatcgtcgc att                                         23

SEQ ID NO: 6         moltype = DNA   length = 20
FEATURE              Location/Qualifiers
misc_feature         1..20
                     note = Reverse primer for TJP1 gene
source               1..20
                     mol_type = other DNA
                     organism = synthetic construct
SEQUENCE: 6
ccaagagccc agttttccat                                             20

SEQ ID NO: 7         moltype = DNA   length = 23
FEATURE              Location/Qualifiers
misc_feature         1..23
                     note = Forward primer for GAPDH gene
source               1..23
                     mol_type = other DNA
                     organism = synthetic construct
SEQUENCE: 7
caaggtcatc catgacaact ttg                                         23

SEQ ID NO: 8         moltype = DNA   length = 22
FEATURE              Location/Qualifiers
misc_feature         1..22
                     note = Reverse primer for GAPDH gene
source               1..22
                     mol_type = other DNA
                     organism = synthetic construct
SEQUENCE: 8
gtccaccacc ctgttgctgt ag                                          22
```

COMPOSITION FOR INHIBITING INTESTINAL PERMEABILITY, TREATING LEAKY GUT RELATED DISEASES AND/OR PREVENTING LEAKY GUT RELATED DISEASES

CROSS REFERENCE TO RELATED APPLICATION

This application is a Divisional of U.S. patent application Ser. No. 17/138,610, filed Dec. 30, 2020 now U.S. Pat. No. 11,701,399, and entitled "COMPOSITION FOR MODULATING INTESTINAL PERMEABILITY AND/OR TREATING AND/OR PREVENTING LEAKY GUT RELATED DISEASES, AND METHOD FOR MODULATING INTESTINAL PERMEABILITY AND/OR TREATING AND/OR PREVENTING LEAKY GUT RELATED DISEASES", which claims priority to U.S. Provisional Application Ser. No. 62/981,720, filed on Feb. 26, 2020 and claims priority of Taiwan Patent Application No. 109146258, filed on Dec. 25, 2020, the entireties of which are incorporated by reference herein.

REFERENCE TO AN ELECTRONIC SEQUENCE LISTING

The contents of the electronic sequence listing (9044B-A2741900-US_ST26_Seq_Listing. xml; Size: 11,205 bytes; and Date of Creation: May 16, 2023) is herein incorporated by reference in its entirety.

TECHNICAL FIELD

The present disclosure relates to a Chinese herbal compound material or a Chinese herbal compound extract, and particularly it relates to a composition for modulating intestinal permeability and/or treating and/or preventing leaky gut related diseases comprising a Chinese herbal compound material or a Chinese herbal compound extract, and use of a Chinese herbal compound material or a Chinese herbal compound extract.

BACKGROUND

The intestinal barrier regulates the stability of the intestinal tract. The main functions thereof include: (1) Water and ion transport: the intestinal tract can process about 9 liters of liquid per day, which is mainly absorbed by the small intestine, and fluid absorption and secretion can be processed through transcellular or intercellular pathways. (2) Regulating antigens: reconciling antigens in the intestinal lumen is the key to maintaining proper immunity. Specific dendritic cells may be activated by changes in intercellular permeability. (3) Immune defense: the intestinal lumen can assist immune defense through the process of flushing microorganisms and toxins (the outer layer of the mucosa contains a large number of bacteria, while the inner layer maintains a sterile state).

The intestinal barrier is mainly composed of several layers of defense mechanism to limit the translocation of antigens in the intestinal lumen. The intestinal barrier comprises a single layer of semipermeable epithelial cells, and the adherent and tight junctions proteins of the apical junctions thereof can join epithelial cells and regulate passing paracellular antigens and molecules through the epithelium. Intestinal epithelial cells transport antigens and molecules from the intestinal lumen to the mucosa via transcellular pathways. Specific epithelial cells, such as M cells (Microfold cells, M cells) can transport antigens in the intestinal lumen to phagocytes and lymphocytes in the epithelium to initiate an immune response. Goblet cells, Paneth cells and enterocytes can secrete mucins and anti-microbial peptides (AMPs) and aggregate into mucosa layer. In addition, the plasma cells of the lamina propria of the intestinal epithelium can secrete IgA. Intestinal epithelial cells also have many microbial recognition receptors (MRR), such as Toll-like receptors (TLRs) and NOD-like receptors, which can identify specific microbial associated molecular patterns (MAMP). The intestinal microbes identified by the intestinal epithelial cells can induce the secretion of cytokines and other immunoregulatory factors, and can help to induce an immune regulatory response to combat the intestinal microbes and maintain the intestinal stability.

The intestinal barrier has the function of preventing the invasion of pathogenic antigens and maintaining intestinal health, and the intestinal flora is an important component of the intestinal mucosal barrier. When the intestinal flora maintains a balance, it can maintain normal body functions. When the intestinal flora is out of balance due to chronic stress, chronic constipation and exposure to environmental toxins (for example, taking antibiotics, unhealthy diet, etc.) to make many bacteria be killed, the intestinal mucosa will be destroyed by bad bacteria to cause food residues and toxins enter the bloodstream, and this phenomenon is leaky gut, or increased intestinal permeability. Leaky gut or increased intestinal permeability can also trigger an inflammatory response.

Leaky gut can be caused by many factors, and can result in many different clinical signs or diseases. Currently known intestinal barrier function abnormalities and intestinal flora imbalance related diseases include inflammatory bowel disease (IBD), celiac disease (coeliac disease), irritable bowel syndrome, acute pancreatitis, non-alcoholic fatty liver disease (NAFLD), alcoholic cirrhosis, type 1 and type 2 diabetes (diabetes mellitus), obesity, chronic kidney disease, cardiovascular disease, multiple organ failure syndrome (shock, burns and trauma), AIDS, asthma, eczema, psoriasis, autism, depression, anxiety, schizophrenia, bipolar disorder, Alzheimer's disease, Parkinson's disease, multiple sclerosis, amyotrophic lateral sclerosis (ALS), ankylosing spondylitis, fibromyalgia, chronic sleep fragmentation, insomnia, etc.

However, so far no Chinese herbal medicine has been verified to be used for the treatment of leaky gut related diseases, and thus there is still an urgent need for novel Chinese herbal medicines for the treatment of leaky gut related diseases.

SUMMARY

The present disclosure provides a composition for modulating intestinal permeability and/or treating and/or preventing leaky gut related diseases, comprising: a Chinese herbal compound material or a Chinese herbal compound extract. The Chinese herbal compound material comprises *Ganoderma*, red jujube, longan, and lotus seed, and in the Chinese herbal compound material, a weight ratio of *Ganoderma*, red jujube, longan and lotus seed is 0.1-15:0.6-2:0.6-2:0.6-5. Moreover, the Chinese herbal compound extract comprises *Ganoderma* extract, red jujube extract, longan extract and lotus seed extract, and a weight ratio of *Ganoderma*, red jujube, longan and lotus seed as preparation raw materials which are respectively needed to obtain the *Ganoderma* extract, the red jujube extract, the longan extract and the lotus seed extract contained in the Chinese herbal compound extract is 0.1-15:0.6-2:0.6-2:0.6-5.

The present disclosure also provides a method for modulating intestinal permeability and/or treating and/or preventing leaky gut related diseases, comprising administering a composition for modulating intestinal permeability and/or treating and/or preventing leaky gut related diseases to a subject in need thereof. The composition for modulating intestinal permeability and/or treating and/or preventing leaky gut related diseases, comprises: a Chinese herbal compound material or a Chinese herbal compound extract. The Chinese herbal compound material comprises *Ganoderma*, red jujube, longan, and lotus seed. Moreover, the Chinese herbal compound extract comprises *Ganoderma* extract, red jujube extract, longan extract and lotus seed extract.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein:

FIG. 3 shows the results of the intestinal epithelial cell permeability test of the compound extract. Compared to the negative control group: *: $p<0.05$; ***: $p<0.001$. Compared to Sample 15A: #: $p<0.05$; ##: $p<0.01$; ###: $p<0.001$. Compared to Sample 1: φ: $p<0.05$, φφ: $p<0.01$, φφφ: $p<0.001$. The data are shown as mean±standard deviation (n=3). The statistical method is one-way ANOVA;

FIGS. 4A to 4D show the results of the intestinal epithelial cell permeability test of the four-ingredient compound extracts with different proportions. Compared to the negative control group: *: $p<0.05$; : $p<0.01$; *: $p<0.001$. Compared to Sample 15A: #:$p<0.05$; ##: $p<0.01$; ###: $p<0.001$. Compared to Sample 1: φ: $p<0.05$, φφ: $p<0.01$, φφφ: $p<0.001$. The data are shown as mean±standard deviation (n=3). The statistical method is one-way ANOVA;

DETAILED DESCRIPTION

Figure 1A:
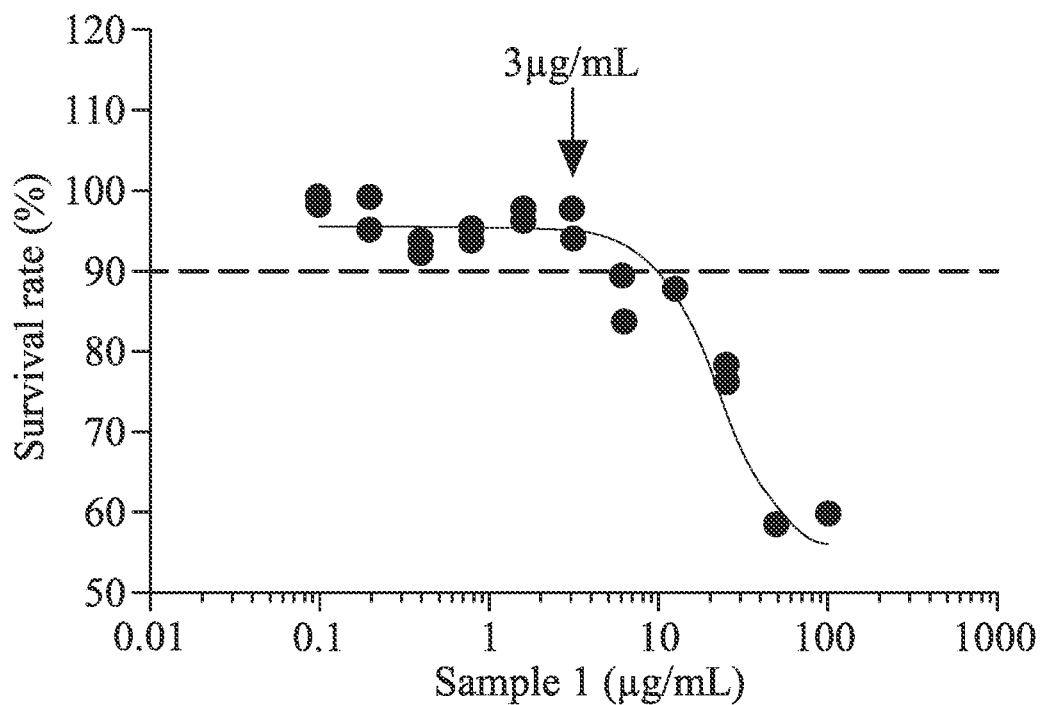
FIGS. 1A to 1P respectively show the results of the cell lethal concentration test of the respective test samples prepared in Example 1.
Figure 1B:
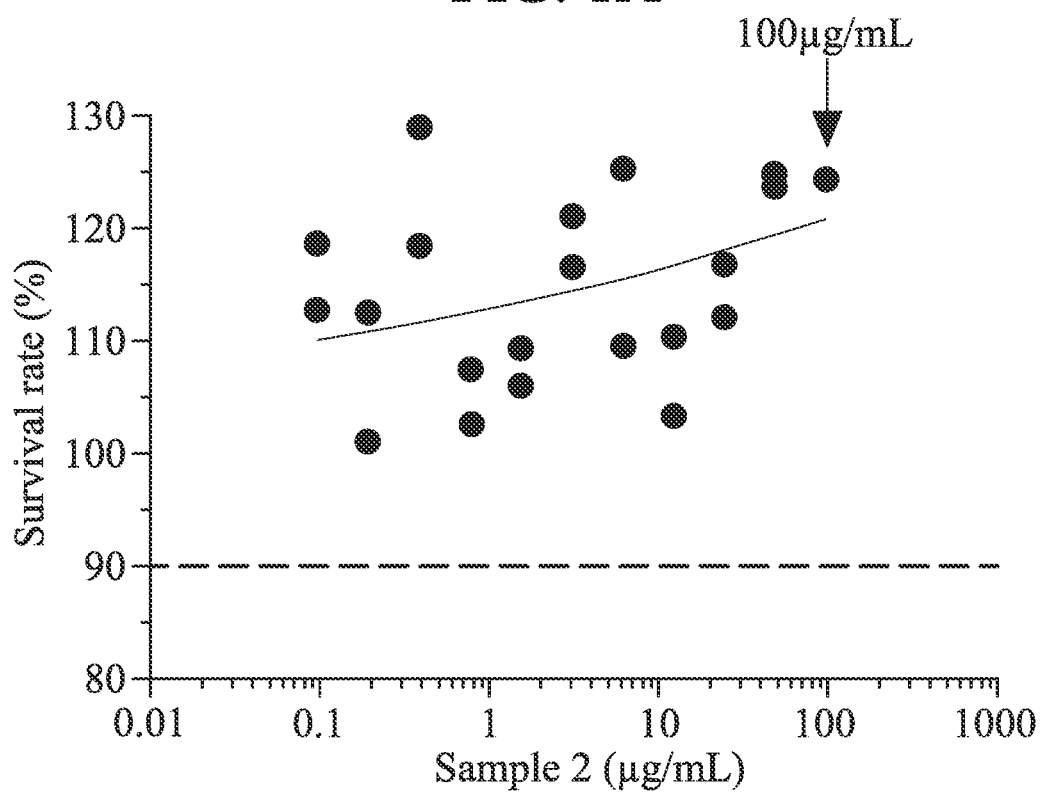
Figure 1C:
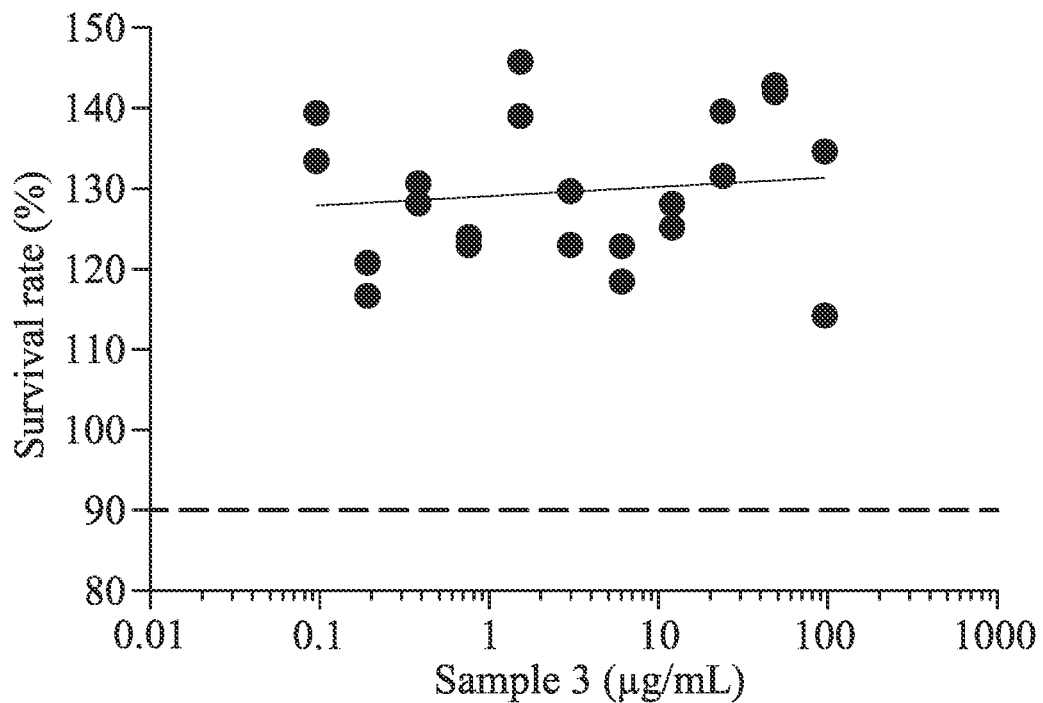
Figure 1D:
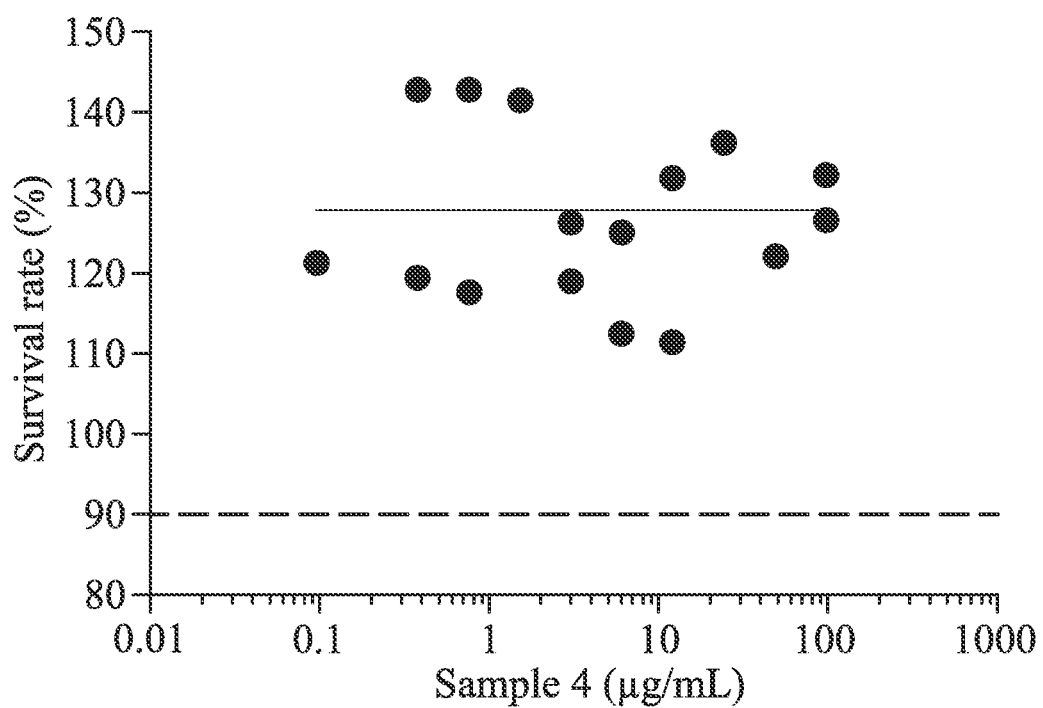
Figure 1E:
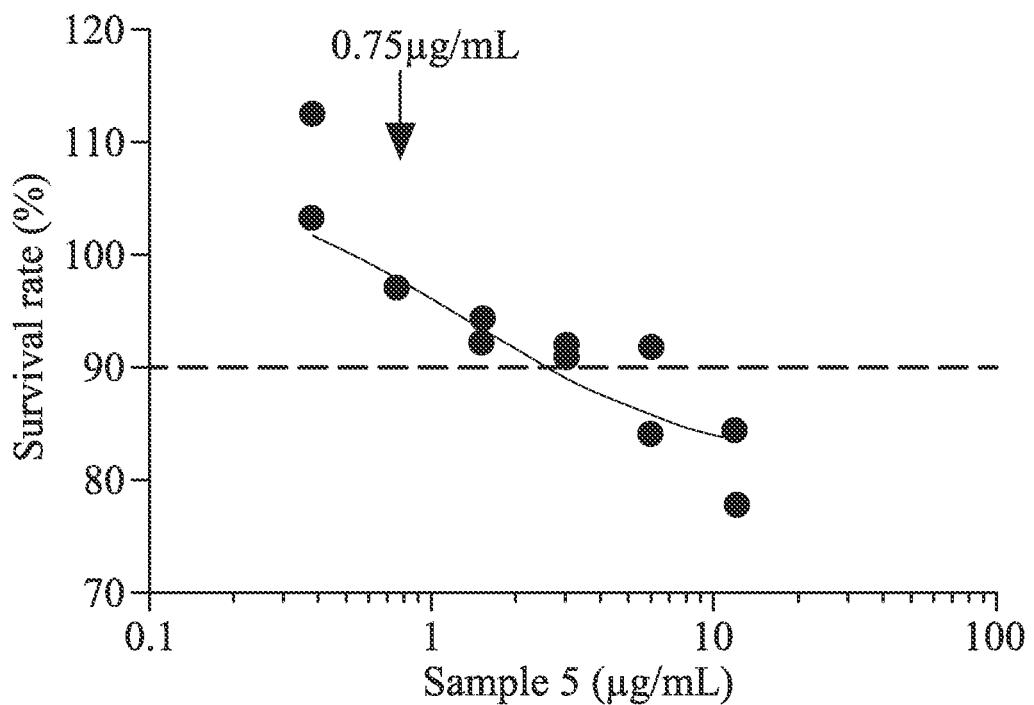
Figure 1F:
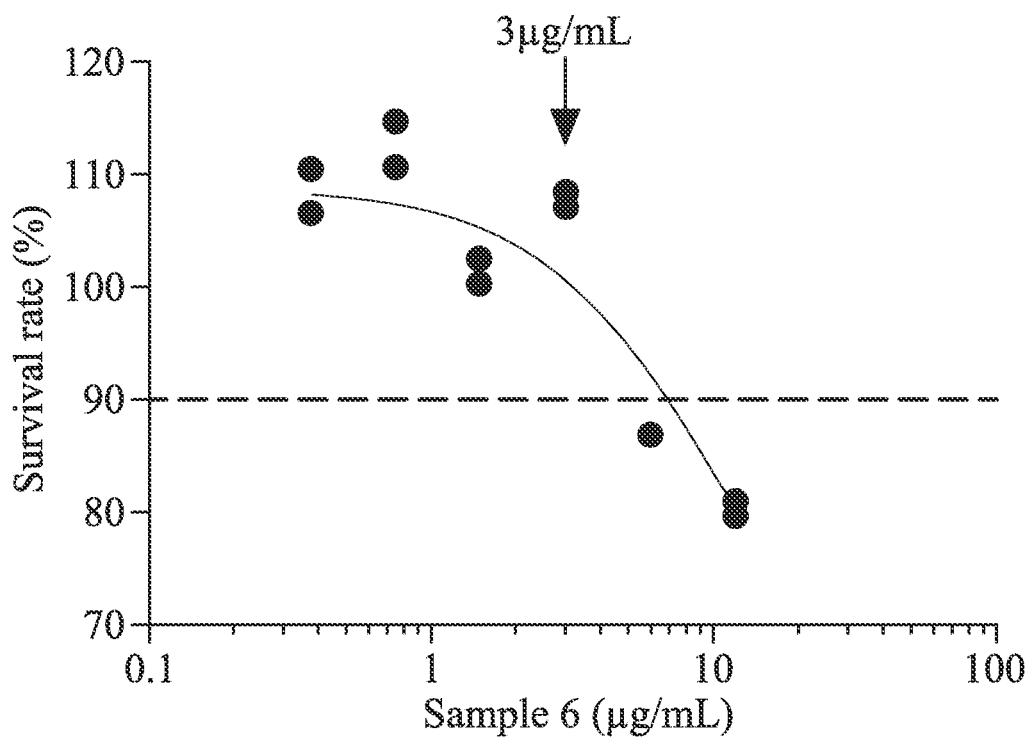
Figure 1G:
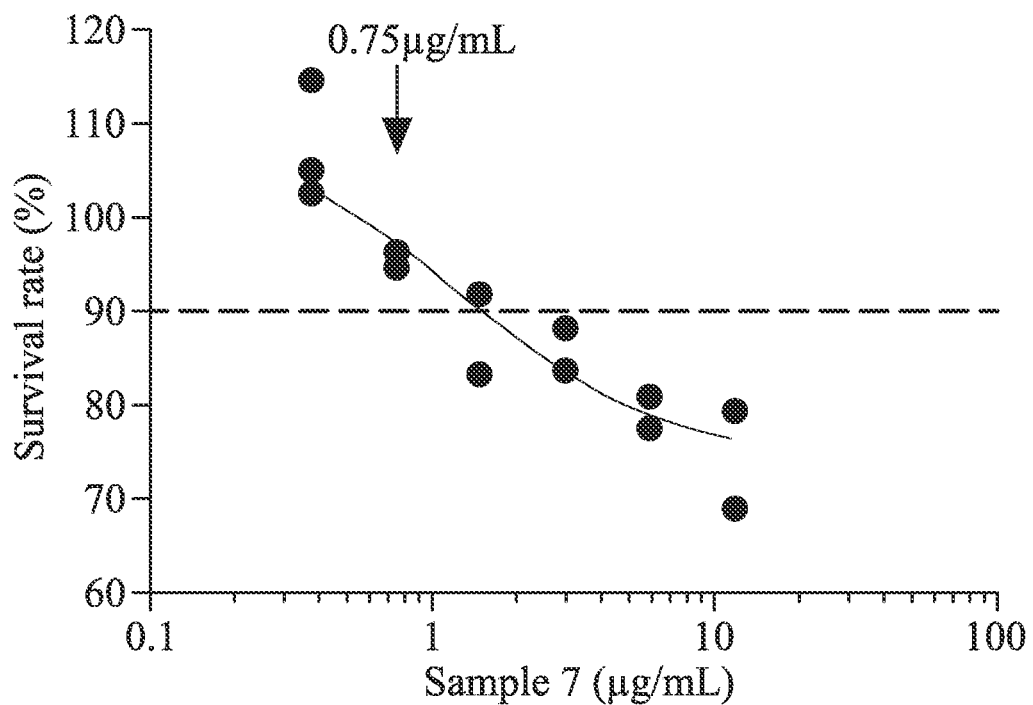
Figure 1H:
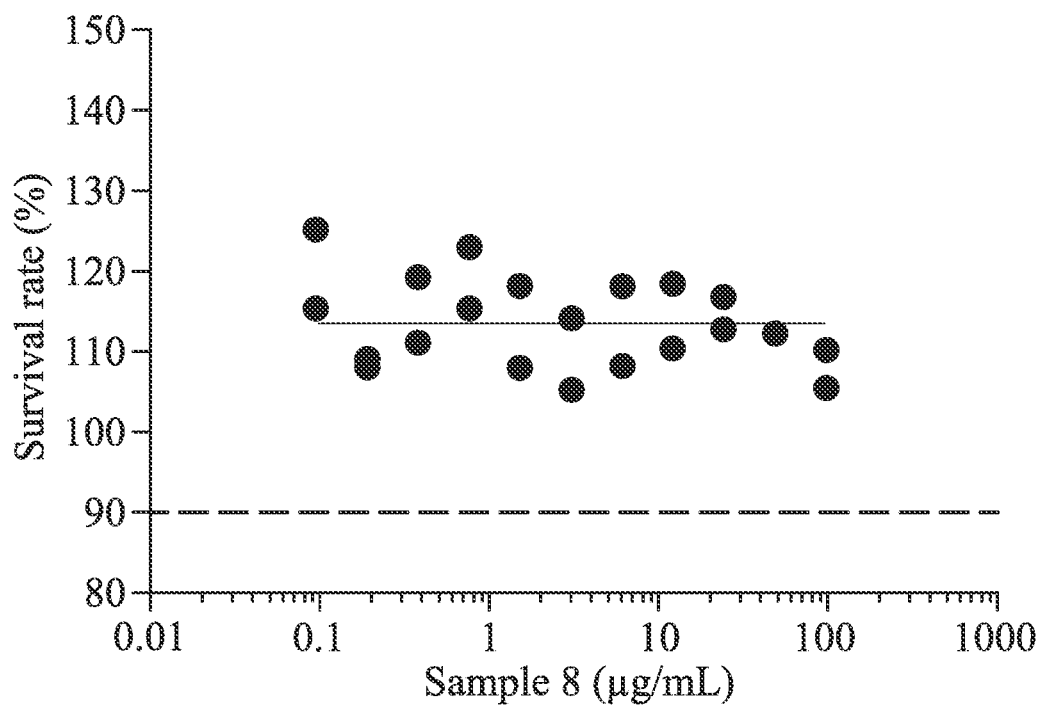
Figure 1I:
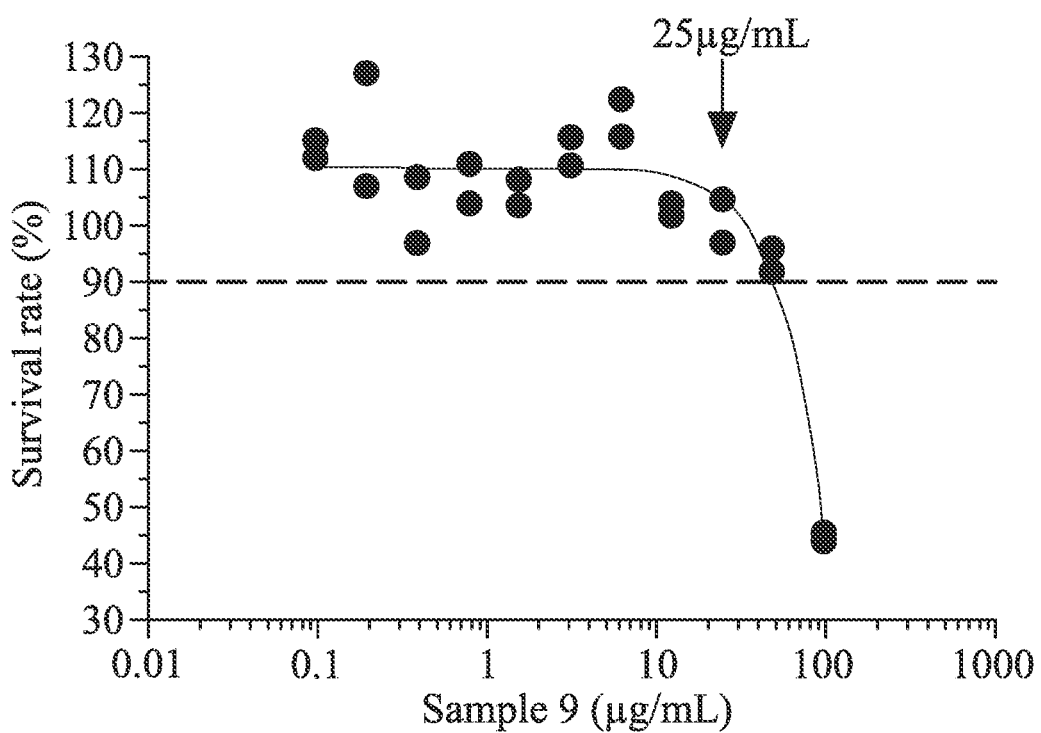
Figure 1J:
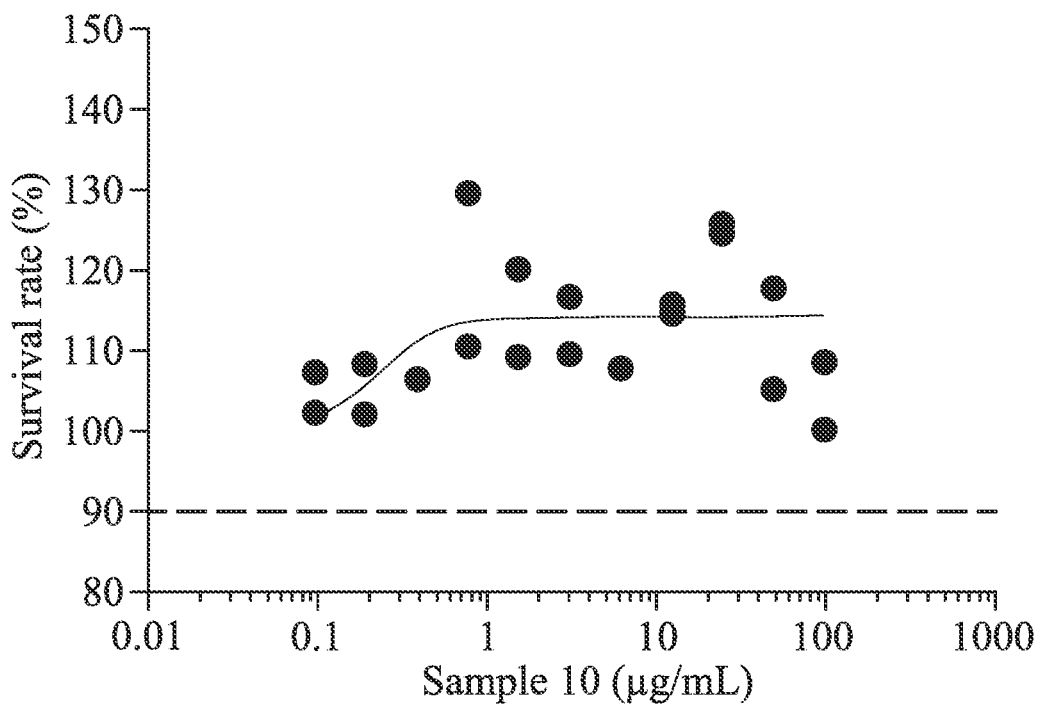
Figure 1K:
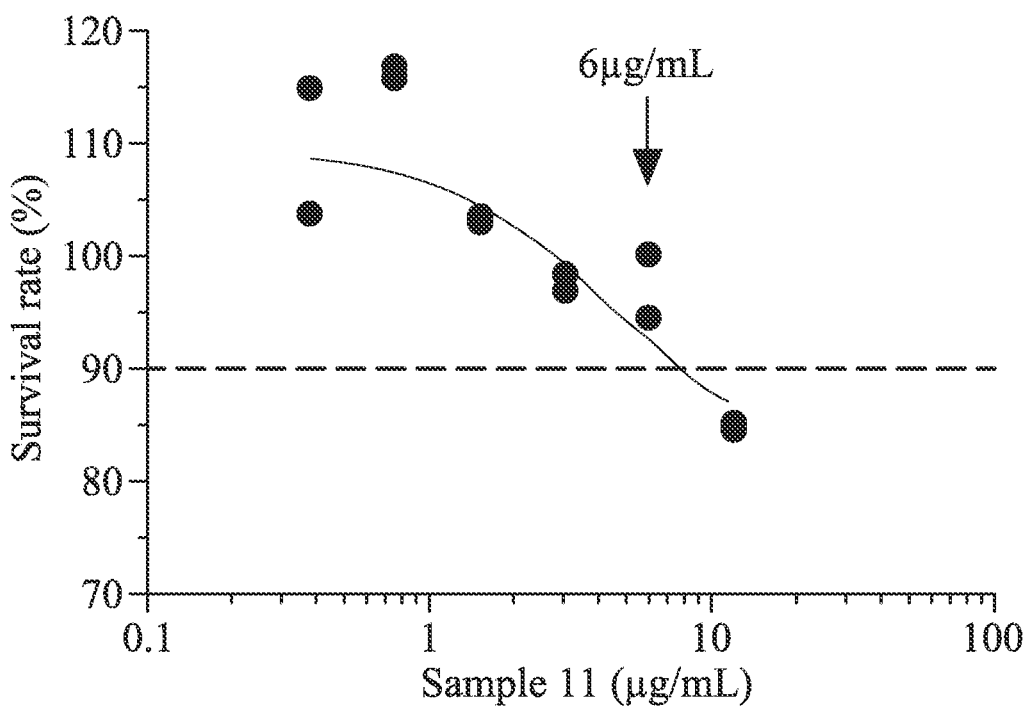
Figure 1L:
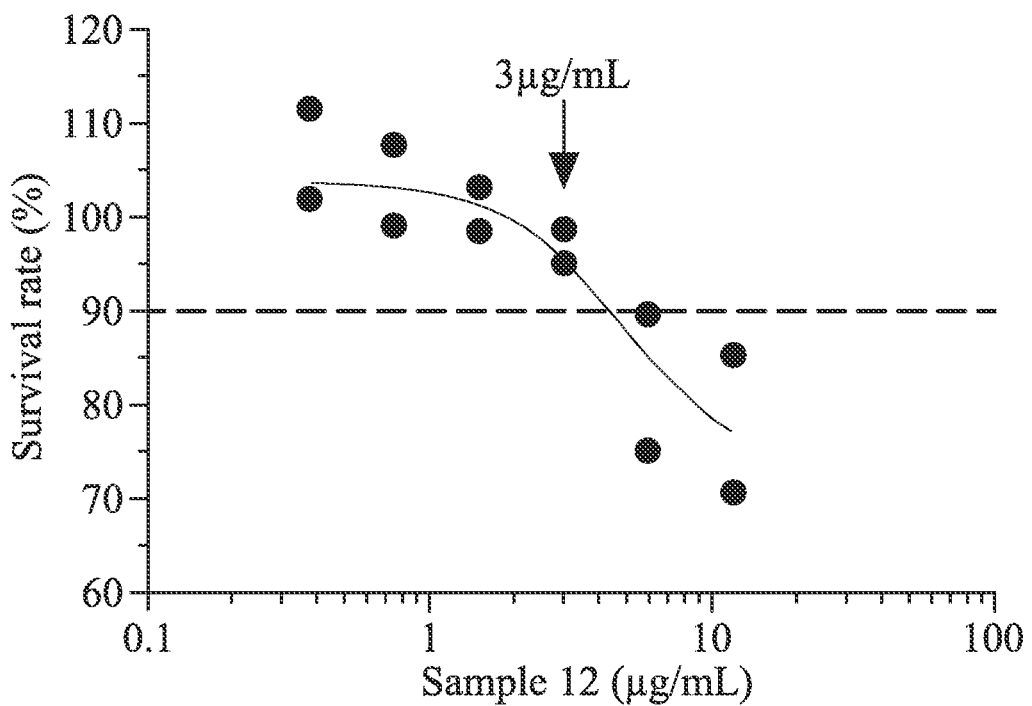
Figure 1M:
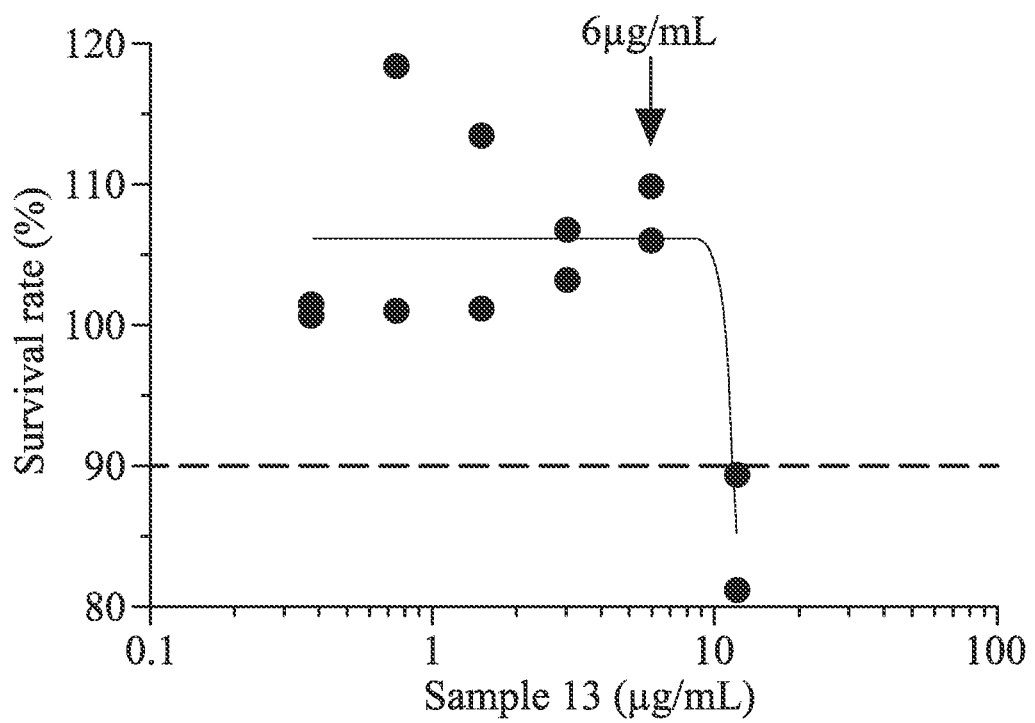
Figure 1N:
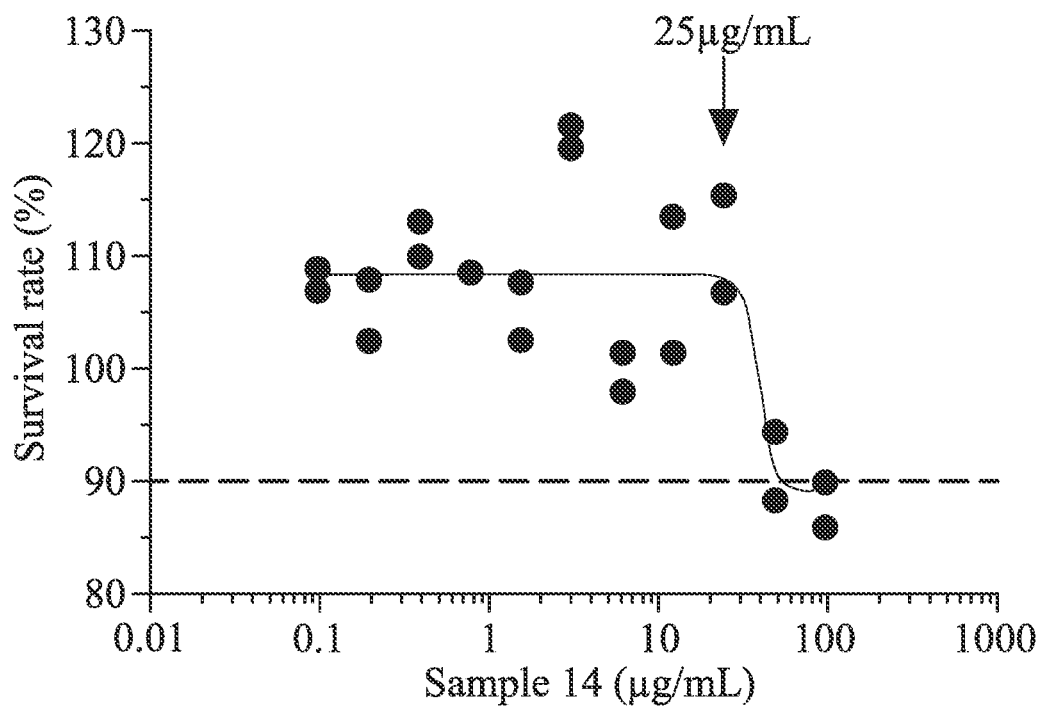
Figure 1O:
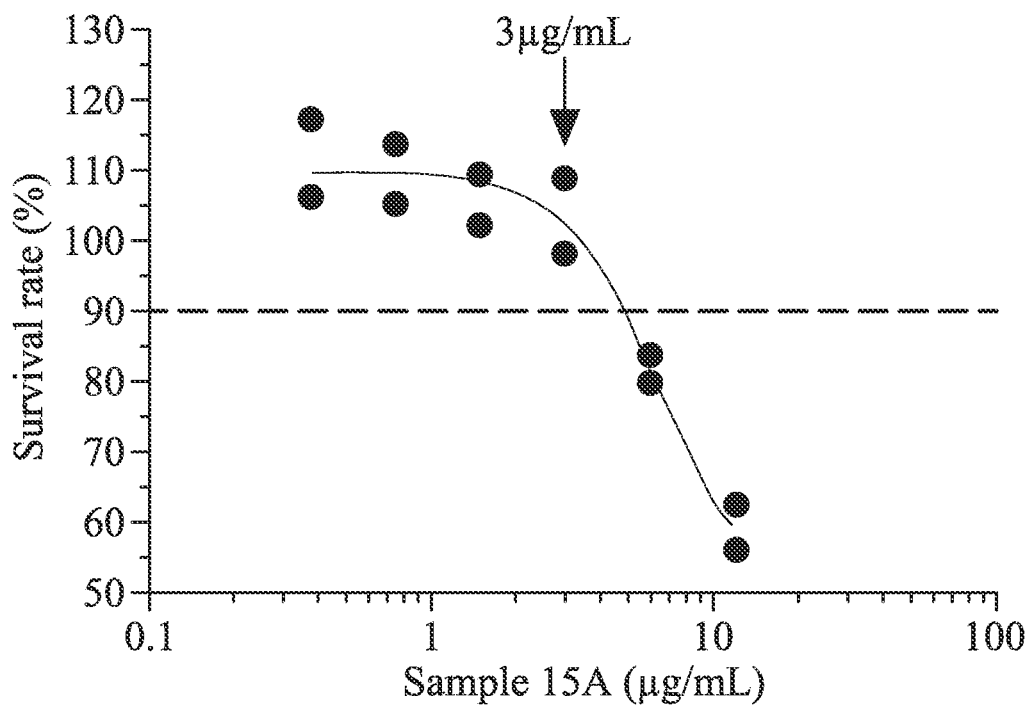

In the following detailed description, for purposes of explanation, numerous specific details are set forth in order to provide a thorough understanding of the disclosed embodiments. It will be apparent, however, that one or more embodiments may be practiced without these specific details.

The present disclosure may provide a composition for modulating intestinal permeability and/or treating and/or preventing leaky gut related diseases, which may comprise, but is not limited to, a Chinese herbal compound material or a Chinese herbal compound extract, but it is not limited thereto.

A "leaky gut related disease" mentioned in the present disclosure is not particularly limited, as long as it is a disease related to leaky gut. For example, a leaky gut related disease may comprise a disease of which a symptom or which itself can be alleviated and/or treated and/or prevented by modulating intestinal permeability and/or by alleviating and/or treating and/or preventing leaky gut, or a disease which is involved in an expression of a gene and/or protein related to leaky gut, and of which a symptom or which itself that can be alleviated and/or treated and/or prevented by modulating the expression of the gene and/or protein related to leaky gut, but it is not limited thereto. Example of the leaky gut related disease may comprise, but is not limited to, inflammatory bowel disease (such as colitis, etc.), celiac disease, irritable bowel syndrome, acute pancreatitis, non-alcoholic steatohepatitis, alcoholic cirrhosis, type 1 diabetes, type 2 diabetes, obesity, chronic kidney disease, cardiovascular disease, multiple organ failure syndrome, AIDS, asthma, eczema, psoriasis, mental disease (such as autism, depression, anxiety, schizophrenia, bipolar disorder, etc.), neurodegenerative disorder (such as Alzheimer's disease, Parkinson's disease, multiple sclerosis, amyotrophic lateral sclerosis or combinations thereof, etc.), ankylosing spondylitis, fibromyalgia, sleep disorder (such as chronic sleep fragmentation, insomnia or a combination thereof) or any combination thereof, etc.

In the composition for modulating intestinal permeability and/or treating and/or preventing leaky gut related diseases of the present disclosure mentioned above, the Chinese herbal compound material mentioned above may comprise, but is not limited to *Ganoderma*, red jujube, longan, and lotus seed, and the Chinese herbal compound extract mentioned above may comprise, but is not limited to, *Ganoderma* extract, red jujube extract, longan extract and lotus seed extract. The Chinese herbal compound material mentioned above or the Chinese herbal compound extract mentioned above has a modulating effect on intestinal permeability and/or has a treating and/or preventing effect on leaky gut related diseases.

In the composition for modulating intestinal permeability and/or treating and/or preventing leaky gut related diseases of the present disclosure, the *Ganoderma* in the Chinese herbal compound material mentioned above or the *Ganoderma* used as one of the preparation raw materials for the Chinese herbal compound extract mentioned above may comprise *Ganoderma lingzhi, Ganoderma sinensis, Ganoderma lucidum* or any combination thereof, but it is not limited thereto. In one embodiment, the *Ganoderma* in the Chinese herbal compound material mentioned above or the *Ganoderma* used as one of the preparation raw materials for the Chinese herbal compound extract mentioned above may be *Ganoderma lucidum*.

In the composition for modulating intestinal permeability and/or treating and/or preventing leaky gut related diseases of the present disclosure, the red jujube in the Chinese herbal compound material mentioned above or the red jujube used as one of the preparation raw materials for the Chinese herbal compound extract mentioned above may comprise grey jujube, jixin jujube, winter jujube, big jujube, small jujube, golden silk jujube or any combination thereof, but it is not limited thereto. In one embodiment, the red jujube in the Chinese herbal compound material mentioned above or the red jujube used as one of the preparation raw materials for the Chinese herbal compound extract mentioned above may be grey jujube.

In the composition for modulating intestinal permeability and/or treating and/or preventing leaky gut related diseases of the present disclosure, the longan in the Chinese herbal compound material mentioned above or the longan used as one of the preparation raw materials for the Chinese herbal compound extract mentioned above may comprise, but is not limited to, Fen Ke longan, Hong Ke longan, Qing Ke longan or any combination thereof. In one embodiment, the longan in the Chinese herbal compound material mentioned above or the used as one of the preparation raw materials for the Chinese herbal compound extract mentioned above may be Fen Ke longan.

Moreover, in the composition for modulating intestinal permeability and/or treating and/or preventing leaky gut related diseases of the present disclosure, the lotus seed in the Chinese herbal compound material mentioned above or the lotus seed used as one of the preparation raw materials for the Chinese herbal compound extract mentioned above may comprise, but is not limited to, red lotus seed, white lotus seed or a combination thereof. In one embodiment, the lotus seed in the Chinese herbal compound material mentioned above or the lotus seed used as one of the preparation raw materials for the Chinese herbal compound extract mentioned above may be red lotus seed.

In one specific embodiment, the *Ganoderma*, red jujube, longan and lotus seed in the Chinese herbal compound material mentioned above or the *Ganoderma*, red jujube, longan and lotus seed used as the preparation raw materials for the Chinese herbal compound extract mentioned above may be *Ganoderma lucidum*, grey jujube, Fen Ke longan and red lotus seed, respectively.

In the composition for modulating intestinal permeability and/or treating and/or preventing leaky gut related diseases of the present disclosure, the composition per gram may at least contains about 0.2 mg of ganoderic acid A, for example, the composition per gram may at least contains about 0.2-20 mg of ganoderic acid A, such as about 0.2 mg, about 0.25 mg, about 0.3 mg, about 0.4 mg, about 0.5 mg, about 0.8 mg, about 1 mg, about 2 mg, about 5 mg, about 10 mg, about 15 mg, about 20 mg, etc., but it is not limited thereto. In one embodiment, the minimum content of the ganoderic acid A mentioned above can be used to confirm the quality of the composition for modulating intestinal permeability and/or treating and/or preventing leaky gut related diseases of the present disclosure.

In one embodiment, in the composition for modulating intestinal permeability and/or treating and/or preventing leaky gut related diseases of the present disclosure, in the Chinese herbal compound material mentioned above, a weight ratio of *Ganoderma*, red jujube, longan and lotus seed may be about 0.1-15:0.6-2:0.6-2:0.6-5, such as about 0.3-12:0.8-1.5:0.8-1.5:0.8-4, about 0.5-10:1:1:1-3, about 1:1:1:1, about 0.5:1:1:1, about 3:1:1:1, about 6:1:1:1, about 10:1:1:1, about 1:1:1:3, but it is not limited thereto. In one specific embodiment, in the composition for modulating intestinal permeability and/or treating and/or preventing leaky gut related diseases of the present disclosure, in the Chinese herbal compound material mentioned above, a weight ratio of *Ganoderma*, red jujube, longan and lotus seed may be 1:1:1:1. In another specific embodiment, in the composition for modulating intestinal permeability and/or treating and/or preventing leaky gut related diseases of the present disclosure, in the Chinese herbal compound material mentioned above, a weight ratio of *Ganoderma*, red jujube, longan and lotus seed may be 3:1:1:1.

In one embodiment, in the composition for modulating intestinal permeability and/or treating and/or preventing leaky gut related diseases of the present disclosure, the form of each herbal material contained in the Chinese herbal compound material mentioned above may comprise original herbal material, slices/pieces obtained by cutting the original herbal material, powder obtained by grinding the original herbal material, etc., or any combination thereof, and it is not particularly limited.

Furthermore, in one embodiment, the composition for modulating intestinal permeability and/or treating and/or preventing leaky gut related diseases of the present disclosure comprises the Chinese herbal compound material mentioned above, and the composition for modulating intestinal permeability and/or treating and/or preventing leaky gut related diseases of the present disclosure can be packaged in a filter bag. In this embodiment, the filter bag packed with composition for modulating intestinal permeability and/or treating and/or preventing leaky gut related diseases of the present disclosure can be brewed with a solvent to obtain brewing liquid. In one specific embodiment, the filter bag packed with composition for modulating intestinal permeability and/or treating and/or preventing leaky gut related diseases of the present disclosure can be brewed with water to obtain brewing liquid which can be taken directly.

Moreover, in one embodiment, in the composition for modulating intestinal permeability and/or treating and/or preventing leaky gut related diseases of the present disclosure, a weight ratio of Ganoderma, red jujube, longan and lotus seed as preparation raw materials which are respectively needed to obtain the Ganoderma extract, the red jujube extract, the longan extract and the lotus seed extract contained in the foregoing Chinese herbal compound extract may be about 0.1-15:0.6-2:0.6-2:0.6-5, such as about 0.3-12:0.8-1.5:0.8-1.5:0.8-4, about 0.5-10:1:1:1-3, about 1:1:1:1, about 0.5:1:1:1, about 3:1:1:1, about 6:1:1:1, about 10:1:1:1, about 1:1:1:3, but it is not limited thereto. In one specific embodiment, in the composition for modulating intestinal permeability and/or treating and/or preventing leaky gut related diseases of the present disclosure, a weight ratio of Ganoderma, red jujube, longan and lotus seed as preparation raw materials which are respectively needed to obtain the Ganoderma extract, the red jujube extract, the longan extract and the lotus seed extract contained in the foregoing Chinese herbal compound extract may be 1:1:1:1. In another specific embodiment, in the composition for modulating intestinal permeability and/or treating and/or preventing leaky gut related diseases of the present disclosure, a weight ratio of Ganoderma, red jujube, longan and lotus seed as preparation raw materials which are respectively needed to obtain the Ganoderma extract, the red jujube extract, the longan extract and the lotus seed extract contained in the foregoing Chinese herbal compound extract may be 3:1:1:1.

Furthermore, in one embodiment, in the composition for modulating intestinal permeability and/or treating and/or preventing leaky gut related diseases of the present disclosure, in the foregoing Chinese herbal compound extract, a weight ratio of the Ganoderma extract mentioned above, the red jujube extract mentioned above, the longan extract mentioned above and the lotus seed extract mentioned above may be about 1-40:20-200:20-180:5-130, such as about 5-35:40-180:40-170:10-120, about 9.3:150.1:136.8:56.2, about 5.3:172.28:156.37:64.25, about 6.18:100.5:91.21:112.45, but it is not limited thereto.

The method for obtaining the Chinese herbal compound extract in the composition for modulating intestinal permeability and/or treating and/or preventing leaky gut related diseases of the present disclosure is not particularly limited, as long as a mixture of all extracts of the herbal materials in the preparation raw material can be obtained.

In one embodiment, the Chinese herbal compound extract in the composition for modulating intestinal permeability and/or treating and/or preventing leaky gut related diseases of the present disclosure may be obtained by a method. The method mentioned above may comprise the following steps, but it is not limited thereto.

First, the respective herbal materials contained in a preparation raw material for forming the preceding Chinese herbal compound extract are respectively subjected an extraction procedure to obtain respective extract solutions of the respective herbal materials. For example, Ganoderma, red jujube, longan and lotus contained in a preparation raw material for forming the preceding Chinese herbal compound extract are respectively subjected an extraction procedure with a solvent to obtain respective Ganoderma extract, red jujube extract, longan extract and lotus seed extract.

Next, the obtained extracts of the respective herbal material are mixed to form a mixture extract to obtain the Chinese herbal compound extract mentioned above. For example, the obtained respective Ganoderma extract, red jujube extract, longan extract and lotus seed extract were mixed to form a mixture extract to obtain the Chinese herbal compound extract mentioned above.

The solvents used in the respective extraction procedures for the respective herbal materials in the preparation raw material can be the same or different, as long as in the subsequent steps of mixing the respective extract solutions, the solvents used in the respective extraction procedures do not affect each other, and do not affect the ingredients in the mixture extract. In one specific embodiment, the solvents used in the respective extraction procedures for the respective herbal materials in the preparation raw material all can be water.

The temperatures for the respective extraction procedures for the respective herbal materials in the preparation raw material can be the same or different, are not particularly limited, and can be adjusted as needed. For example, the temperatures for the respective extraction procedures for the respective herbal materials can be adjusted according to the environment (such as environmental temperature, humidity, and pressure) at the time at which the extraction procedure is performed, the kind of herbal material to be extracted, the condition of the herbal material (such as moisture content, and weight) to be extracted, the extraction time to be performed, and/or the kind of extraction solvent to be used, but they are not limited thereto. For example, the temperatures for the respective extraction procedures for the respective herbal materials in the preparation raw material are above the freezing point and below the boiling point of the solvents used in the respective extraction procedures. In one embodiment, the solvents used in the respective extraction procedures for the respective herbal materials in the preparation raw material all are water, and the temperatures for the respective extraction procedures for the respective herbal materials in the preparation raw material may be about 0-100° C., such as about 4° C., about 5° C., about 10° C., about 15° C., about 20° C., about 25° C., about 30° C., about 35° C., about 37° C., about 40° C., about 50° C., about 60° C., about 70° C., about 80° C., about 90° C., and about 100° C., but it is not limited thereto.

Similarly, the time for performing the respective extraction procedures for the respective herbal materials in the preparation raw material can be the same or different, is not particularly limited, and can be adjusted as needed. For example, the time for the respective extraction procedures for the respective herbal materials can be adjusted according to the environment (such as environmental temperature, humidity, and pressure) at the time at which the extraction procedure is performed, the kind of herbal material to be extracted, the condition of the herbal material (such as moisture content, and weight) to be extracted, the extraction temperature to be adopted, and/or the kind of extraction solvent to be used, but it is not limited thereto. For example, the time for performing the respective extraction procedures for the respective herbal materials in the preparation raw material may be about 0.1-10 hours, such as about 0.1 hour, about 0.5 hour, about 1 hour, about 1.5 hours, about 2 hours, about 2.5 hours, about 5 hours, about 8 hours, and about 10 hours, but it is not limited thereto. In one embodiment, the solvents used in the respective extraction procedures for the respective herbal materials in the preparation raw material all are water, and the time for performing the respective extraction procedures for the respective herbal materials in the preparation raw material may be about 0.1-10 hours, such as about 0.1 hour, about 0.5 hour, about 1 hour, about 1.5 hours, about 2 hours, about 2.5 hours, about 5 hours, about 8 hours, and about 10 hours, but it is not limited thereto.

In addition, according to needs, after the step of mixing the obtained extracts of respective herbal material to form a mixture extract, the above-mentioned method for obtaining the Chinese herbal compound extract in the composition for modulating intestinal permeability and/or treating and/or preventing leaky gut related diseases of the present disclosure may further comprise a step of drying the mixture extract mentioned above. The method for drying is not particularly limited, as long as the extract can be dried, such as oven drying, and freeze drying. In one embodiment, the mixture extract is dried by freeze drying.

Furthermore, in another embodiment, the Chinese herbal compound extract in the composition for modulating intestinal permeability and/or treating and/or preventing leaky gut related diseases of the present disclosure may be obtained by another method. The method mentioned above may comprise the following steps, but it is not limited thereto.

First, the respective herbal materials contained in a preparation raw material for forming the preceding Chinese herbal compound extract are mixed to form a raw material mixture. For example, *Ganoderma*, red jujube, longan and lotus seed contained in a preparation raw material for forming the preceding Chinese herbal compound extract are mixed to form a raw material mixture.

Next, the foregoing raw material mixture is subjected an extraction procedure to obtain a mixture extract. For example, a raw material mixture containing *Ganoderma*, red jujube, longan and lotus seed is subjected an extraction procedure to obtain a mixture extract to obtain the Chinese herbal compound extract mentioned above.

The solvent used in the extraction procedure for the raw material mixture is not particularly limited, and can be adjusted as needed, as long as it has no adverse effect on the ingredients in the extract. In one specific embodiment, the solvent used in the extraction procedure for the raw material mixture can be water.

The temperature for the extraction procedure for the raw material mixture is not particularly limited, and can be adjusted as needed. For example, the temperature for the extraction procedure for the raw material mixture can be adjusted according to the environment (such as environmental temperature, humidity, and pressure) at the time at which the extraction procedure is performed, the kinds of herbal materials contained in the raw material mixture to be extracted, the condition of the raw material mixture (such as moisture content, and weight) to be extracted, the extraction time to be performed, and/or the kind of extraction solvent to be used, but it is not limited thereto. For example, the temperature for the extraction procedure for the raw material mixture is above the freezing point and below the boiling point of the solvent used in the extraction procedure. In one embodiment, the solvent used in the extraction procedure for the raw material mixture is water, and the temperature for the extraction procedure for the raw material mixture may be about 0-100° C., such as about 4° C., about 5° C., about 10° C., about 15° C., about 20° C., about 25° C., about 30° C., about 35° C., about 37° C., about 40° ° C., about 50° C., about 60° C., about 70° ° C., about 80° C., about 90° C., and about 100° C., but it is not limited thereto.

Similarly, the time for performing the extraction procedure for the raw material mixture is not particularly limited, and can be adjusted as needed. For example, the time for performing the extraction procedure for the raw material mixture can be adjusted according to the environment (such as environmental temperature, humidity, and pressure) at the time at which the extraction procedure is performed, the kinds of herbal materials contained in the raw material mixture to be extracted, the condition of the raw material mixture (such as moisture content, and weight) to be extracted, the extraction temperature to be adopted, and/or the kind of extraction solvent to be used, but it is not limited thereto. For example, the time for performing the extraction procedure for the raw material mixture may be about 0.1-10 hours, such as about 0.1 hour, about 0.5 hour, about 1 hour, about 1.5 hours, about 2 hours, about 2.5 hours, about 5 hours, about 8 hours, and about 10 hours, but it is not limited thereto. In one embodiment, the solvent used in the extraction procedure for the raw material mixture is water, and the time for performing the extraction procedure for the raw material mixture may be about 0.1-10 hours, such as about 0.1 hour, about 0.5 hour, about 1 hour, about 1.5 hours, about 2 hours, about 2.5 hours, about 5 hours, about 8 hours, and about 10 hours, but it is not limited thereto.

In addition, according to needs, after the step of mixing the obtained extracts of respective herbal material to form a mixture extract, the above-mentioned method for obtaining the Chinese herbal compound extract in the composition for modulating intestinal permeability and/or treating and/or preventing leaky gut related diseases of the present disclosure may further comprise a step of drying the mixture extract mentioned above. The method for drying is not particularly limited, as long as the extract can be dried, such as oven drying, and freeze drying. In one embodiment, the mixture extract is dried by freeze drying.

In one embodiment, the composition for modulating intestinal permeability and/or treating and/or preventing leaky gut related diseases of the present disclosure mentioned above, in addition to the foregoing Chinese herbal compound material or the Chinese herbal compound extract, may further comprise a pharmaceutically acceptable carrier or salt, but it is not limited thereto. In this embodiment, in the composition for modulating intestinal permeability and/or treating and/or preventing leaky gut related diseases of the present disclosure mentioned above, the content of the foregoing Chinese herbal compound material or the Chinese herbal compound extract may be about 10-99.5 wt %, such as about 10-50 wt %, and about 50-99.5 wt %, but it is not limited thereto. In this embodiment, the composition for modulating intestinal permeability and/or treating and/or preventing leaky gut related diseases of the present disclosure mentioned above may be a pharmaceutical composition or a health care composition, but it is not limited thereto.

The pharmaceutically acceptable carrier mentioned above may comprise, but is not limited to, a solvent, a dispersion medium, a coating, an antibacterial and antifungal agent, or an isotonic and absorption delaying agent, etc. which is suitable for pharmaceutical administration. The pharmaceutical composition can be formulated into dosage forms for different administration routes utilizing conventional methods.

Moreover, the pharmaceutically acceptable salt mentioned above may comprise, but is not limited to, salts including inorganic cation, such as alkali metal salts such as sodium salt, potassium salt or amine salt, such as alkaline-earth metal salt such as magnesium salt or calcium salt, such as the salt containing bivalent or quadrivalent cation such as zinc salt, aluminum salt or zirconium salt. Furthermore, the pharmaceutically acceptable salt may also be organic salt, such as dicyclohexylamine salt, methyl-D-glucamine, and amino acid salt such as arginine, lysine, histidine, or glutamine.

Furthermore, example for the composition for modulating intestinal permeability and/or treating and/or preventing leaky gut related diseases of the present disclosure mentioned above may comprise, but is not limited to, a pharmaceutical composition or a health care composition, but it is not limited thereto.

The pharmaceutical composition or a health care composition of the present disclosure may be administered parenterally, orally, by an inhalation spray, or via an implanted reservoir. The parenteral methods may comprise smearing on skin on any region or a region needed thereof, subcutaneous, intracutaneous, intravenous, intramuscular, intra-articular, intra-arterial, intrasynovial, intrasternal, intrathecal, intralesional injection, as well as infusion techniques.

The oral form of the pharmaceutical composition or health care composition mentioned in the present disclosure may comprise tablets, granules, powders, pellet in capsules, capsules, coated tablets, emulsions, solutions, aqueous suspensions, dispersions, instant powders, etc., but it is not limited thereto.

In one specific embodiment, the composition for modulating intestinal permeability and/or treating and/or preventing leaky gut related diseases of the present disclosure mentioned above may be a pharmaceutical composition. In this specific embodiment, the pharmaceutical composition may be an oral dosage form, wherein the oral dosage form may comprise tablets, granules, powders, pellet in capsules, capsules, coated tablets, emulsions, solutions, aqueous suspensions, dispersions, etc., but it is not limited thereto. Moreover, in this specific embodiment, the pharmaceutical composition may comprise, but is not limited to a pharmaceutical composition for treating and/or preventing inflammatory bowel diseases, neurodegenerative disorders and/or sleep disorder.

In another specific embodiment, the composition for modulating intestinal permeability and/or treating and/or preventing leaky gut related diseases of the present disclosure mentioned above may be a health care composition. In this specific embodiment, the health care composition may be a health food, wherein the form of the health food may comprise tablets, granules, powders, pellet in capsules, capsules, coated tablets, emulsions, solutions, aqueous suspensions, dispersions, instant powders, etc., but it is not limited thereto. Moreover, in this specific embodiment, the health care composition may comprise, but is not limited to, a health care composition for preventing and/or ameliorating inflammatory bowel diseases, neurodegenerative disorders and/or sleep disorder.

Based on the foregoing, the present disclosure may further provide a use of a Chinese herbal compound material or a Chinese herbal compound extract in the manufacture of a composition for modulating intestinal permeability and/or treating and/or preventing leaky gut related diseases.

Moreover, the present disclosure can further provide a use of a Chinese herbal compound material or a Chinese herbal compound extract in the manufacture of a composition for treating and/or preventing inflammatory bowel diseases. The inflammatory bowel disease mentioned herein may comprise, but is not limited to, colitis, etc. In one embodiment, the inflammatory bowel disease mentioned herein is colitis.

Furthermore, the present disclosure may further provide a use of a Chinese herbal compound material or a Chinese herbal compound extract in the manufacture of a composition for treating and/or preventing neurodegenerative disorders. The neurodegenerative disorder mentioned herein may comprise, but is not limited to, Alzheimer's disease, Parkinson's disease, multiple sclerosis, amyotrophic lateral sclerosis or combinations thereof, etc. In one embodiment, the inflammatory bowel disease mentioned herein is Alzheimer's disease.

The present disclosure may yet further provide a use of a Chinese herbal compound material or a Chinese herbal compound extract in the manufacture of a composition for treating and/or preventing sleep disorders. The sleep disorder mentioned herein may comprise, but is not limited to, chronic sleep fragmentation, insomnia or a combination thereof, etc. In one embodiment, the sleep disorder mentioned herein is insomnia.

In the respective uses of a Chinese herbal compound material or a Chinese herbal compound extract of the present disclosure mentioned above, the foregoing Chinese herbal compound material or the foregoing Chinese herbal compound extract mentioned above has a modulating effect on intestinal permeability and/or has a treating and/or preventing effect on leaky gut related diseases.

Furthermore, all related interpretations for the Chinese herbal compound material or the Chinese herbal compound extract involved in the respective uses of the present disclosure mentioned above can be referred to the description related to the Chinese herbal compound material or the Chinese herbal compound extract in the proceeding paragraphs for interpreting the composition for modulating intestinal permeability and/or treating and/or preventing leaky gut related diseases of the present disclosure, and thus are not repeated herein.

In one embodiment, in the respective uses of a Chinese herbal compound material or a Chinese herbal compound extract of the present disclosure mentioned above, a pharmaceutically acceptable carrier or salt may be further used in a preparation for the composition for modulating intestinal permeability and/or treating and/or preventing leaky gut related diseases.

Related interpretations for the pharmaceutically acceptable carrier or salt can be also referred to the related description in the proceeding paragraphs for interpreting the composition for modulating intestinal permeability and/or treating and/or preventing leaky gut related diseases of the present disclosure, and thus are not repeated herein.

Furthermore, all related interpretations for the composition manufactured in the respective uses of the present disclosure can be referred to all description in the proceeding paragraphs for interpreting the composition for modulating intestinal permeability and/or treating and/or preventing leaky gut related diseases of the present disclosure, but it is not limited thereto.

In addition, based on the foregoing, the present disclosure may further provide a method for modulating intestinal permeability and/or treating and/or preventing leaky gut related diseases. The method mentioned above may comprise, but is not limited to, administering any composition for modulating intestinal permeability and/or treating and/or preventing leaky gut related diseases of the present disclosure mentioned above to a subject in need thereof.

Moreover, based on the foregoing, the present disclosure may further provide a method for treating and/or preventing inflammatory bowel diseases. The method mentioned above may comprise, but is not limited to, administering any composition for modulating intestinal permeability and/or treating and/or preventing leaky gut related diseases of the present disclosure mentioned above to a subject in need thereof. The inflammatory bowel disease mentioned herein may comprise, but is not limited to, colitis, etc.

Based on the foregoing, the present disclosure may also provide a method for treating and/or preventing neurodegenerative disorders. The method mentioned above may comprise, but is not limited to, administering any composition for modulating intestinal permeability and/or treating and/or preventing leaky gut related diseases of the present disclosure mentioned above to a subject in need thereof. The neurodegenerative disorder mentioned herein may comprise, but is not limited to, Alzheimer's disease, Parkinson's disease, multiple sclerosis, amyotrophic lateral sclerosis or combinations thereof, etc.

Based on the foregoing, the present disclosure may also provide a method for treating and/or preventing sleep disorders. The method mentioned above may comprise, but is not limited to, administering any composition for modulating intestinal permeability and/or treating and/or preventing leaky gut related diseases of the present disclosure mentioned above to a subject in need thereof. The sleep disorder mentioned herein may comprise chronic sleep fragmentation, insomnia or a combination thereof, etc., but it is not limited thereto.

The subject mentioned in the present disclosure may comprise, but is not limited to, a vertebrate. The vertebrate mentioned above may comprise a fish, an amphibian, a reptile, a bird or a mammal, but it is not limited thereto. Example of the mammal may comprise, but is not limited to a human, an orangutan, a monkey, a horse, a donkey, a dog, a cat, a rabbit, a guinea pig, a rat, a mouse, etc. In one embodiment, the said subject may be a human.

EXAMPLES

Example 1: Preparation of Test Samples 40 g of *Ganoderma lucidum*, 40 g of grey jujube, 40 g of Fen Ke longan and 40 g of red lotus seed were refluxed and extracted with 400 g of water for 2 hours, respectively, to obtain a *Ganoderma lucidum* extract solution (i) (241 g), a red jujube extract solution (ii) (338 g), a longan extract solution (iii) (286 g) and a lotus seed extract solution (iv) (313 g).

The extracts of the respective herbal materials were taken by the weight corresponding to the contents (proportions) of the respective herbal materials in the preparation raw material in the condition of that the total weight of the respective herbal materials in the preparation raw materials was set to 1 g, and mixed to prepare 16 test samples shown in the following Table 1.

TABLE 1

| Sample number | Herbal material contained in the preparation raw material | Weight ratio of herbal materials contained in the preparation raw material |
|---|---|---|
| 1 | Ganoderma | — |
| 2 | Red jujube | — |
| 3 | Longan | — |
| 4 | Lotus seed | — |
| 5 | Ganoderma and red jujube | 1:1 |
| 6 | Ganoderma and longan | 1:1 |
| 7 | Ganoderma and lotus seed | 1:1 |
| 8 | Red jujube and longan | 1:1 |
| 9 | Red jujube and lotus seed | 1:1 |
| 10 | Longan and lotus seed | 1:1 |
| 11 | Ganoderma, red jujube and longan | 1:1:1 |
| 12 | Ganoderma, red jujube, and lotus seed | 1:1:1 |
| 13 | Ganoderma, longan and lotus seed | 1:1:1 |
| 14 | Red jujube, longan and lotus seed | 1:1:1 |
| 15A | Ganoderma, red jujube, longan and lotus seed | 1:1:1:1 |
| 15B | Ganoderma, red jujube, longan and lotus seed | 3:1:1:1 |
| 15C | Ganoderma, red jujube, longan and lotus seed | 0.5:1:1:1 |
| 15D | Ganoderma, red jujube, longan and lotus seed | 6:1:1:1 |
| 15E | Ganoderma, red jujube, longan and lotus seed | 10:1:1:1 |
| 15F | Ganoderma, red jujube, longan and lotus seed | 1:0.5:1:1 |
| 15G | Ganoderma, red jujube, longan and lotus seed | 1:3:1:1 |
| 15H | Ganoderma, red jujube, longan and lotus seed | 1:6:1:1 |
| 15I | Ganoderma, red jujube, longan and lotus seed | 1:10:1:1 |
| 15J | Ganoderma, red jujube, longan and lotus seed | 1:1:0.5:1 |
| 15K | Ganoderma, red jujube, longan and lotus seed | 1:1:3:1 |
| 15L | Ganoderma, red jujube, longan and lotus seed | 1:1:6:1 |
| 15M | Ganoderma, red jujube, longan and lotus seed | 1:1:10:1 |
| 15N | Ganoderma, red jujube, longan and lotus seed | 1:1:1:0.5 |
| 15O | Ganoderma, red jujube, longan and lotus seed | 1:1:1:3 |
| 15P | Ganoderma, red jujube, longan and lotus seed | 1:1:1:6 |
| 15Q | Ganoderma, red jujube, longan and lotus seed | 1:1:1:10 |

For example, for a single-ingredient sample of *Ganoderma lucidum*, namely, the *Ganoderma lucidum* extract solution (i) obtained in the foregoing was taken by an amount of 1/40 weight thereof (241 g*(1/40)=6.025 g) (corresponding to 1 g of herbal material of *Ganoderma lucidum*) and freeze dried.

For example, for a combination sample with two-ingredient compound of *Ganoderma lucidum* and red jujube, namely, the *Ganoderma lucidum* extract solution (i) obtained in the foregoing was taken by an amount of 1/80 weight thereof (241 g*(1/80)=3.013 g) and the red jujube extract solution (ii) obtained in the foregoing was taken by an amount of 1/80 weight thereof (338 g*(1/80)=4.225 g) (corresponding to 0.5 g herbal material of *Ganoderma lucidum* and 0.5 g herbal material of red jujube, the total weight of the respective herbal materials was 1 g), and the two were well mixed and freeze dried.

For example, for a combination sample with three-ingredient compound of *Ganoderma lucidum*, red jujube and longan, namely, the *Ganoderma lucidum* extract solution (i) obtained in the foregoing was taken by an amount of 1/120 weight thereof (241 g*(1/120)=2.008 g), the red jujube extract solution (ii) obtained in the foregoing was taken by an amount of 1/120 weight thereof (338 g*(1/120)=2.817 g) and the longan extract solution (iii) obtained in the foregoing was taken by an amount of 1/120 weight thereof (286 g*(1/120) =2.383 g) (corresponding to 0.33 g herbal material of *Ganoderma lucidum,* 0.33 g herbal material of red jujube, and 0.33 g herbal material of longan, the total weight of the respective herbal material was 1 g), and the three were well mixed and freeze dried.

For a combination sample with four-ingredient compound of *Ganoderma lucidum,* red jujube, longan and lotus seed (1:1:1:1), namely, the *Ganoderma lucidum* extract solution (i) obtained in the foregoing was taken by an amount of 1/160 weight thereof (241 g*(1/160)=1.506 g), the red jujube extract solution (ii) obtained in the foregoing was taken by an amount of 1/160 weight thereof (338 g*(1/160)=2.113 g), the longan extract solution (iii) obtained in the foregoing was taken by an amount of 1/160 weight thereof (286 g*(1/160)=1.788 g) and the lotus seed extract solution (iv) obtained in the foregoing was taken by an amount of 1/160 weight thereof (313 g*(1/160)=1.956 g) (corresponding to 0.25 g herbal material of *Ganoderma lucidum,* 0.25 g herbal material of red jujube, 0.25 g herbal material of longan and 0.25 g herbal material of lotus seed, the total weight of the respective herbal material was 1 g).

The 16 test samples shown in Table 1 were prepared according to the rules described above.

The dry weight of the respective medicinal extracts contained in the respective test samples can be inferred, for example, according to the estimation method shown in Table 2-5 below. Moreover, based on the dry weight of the respective extracts corresponding to that is obtained from 1 g of the respective herbal materials shown in Tables 2-5 below, the extractabilities for the respective extracts can be calculated by the following formula.

Extractability (%)=Dry weight of extract/Weight of the corresponding herbal material*100

Extractabilities for the respective extracts are shown in the following:

Extractability for the *Ganoderma* extract: 3.71% (0.0371 g/1 g*100)

Extractability for the red jujube extract: 60.3% (0.603 g/1 g*100)

Extractability for the longan extract: 54.73% (0.5473 g/1 g*100)

Extractability for the lotus seed extract: 22.49% (0.225 g/1 g*100)

TABLE 2

Illustrative estimation method for dry weights of extracts of the respective herbal materials contained in a test sample with two-ingredient compound

| Sample number | Herbal materials contained in preparation raw material | Weight ratio of Herbal materials contained in 1 g perparation raw material | Dry weight of sample | Ganoderma extract | Red jujube extract | Longan extract | Lotus seed extract |
|---|---|---|---|---|---|---|---|
| 1 | Ganoderma | — | 37.1 | 37.1 | — | — | — |
| 2 | Red jujube | — | 603 | — | 603 | — | — |
| 3 | Longan | — | 547.3 | — | — | 547.3 | — |
| 4 | Lotus seed | — | 224.9 | — | — | — | 224.9 |
| 6 | Ganoderma and longan | 1:1 | 292.2 | 37.1*1/2 = 18.6 | — | 547.3*1/2 = 273.7 | — |

Note:
Dry weight of Test ample 6, 292.2 mg ≒ Estimated dry weight of Ganoderma extract contained therein, 18.6 mg + Estimated dry weight of longan extract contained therein, 273.7 mg

TABLE 3

Illustrative estimation method for dry weights of extracts of the respective herbal materials contained in a test sample with three-ingredient compound

| Sample number | Herbal materials containted in preparation raw material | Weight ratio of Herbal materials contained in 1 g preparation raw material | Dry weight of sample | Ganoderma extract | Red jujube extract | Longan extract | Lotus seed extract |
|---|---|---|---|---|---|---|---|
| 1 | Ganoderma | — | 37.1 | 37.1 | — | — | — |
| 2 | Red jujube | — | 603 | — | 603 | — | — |
| 3 | Longan | — | 547.3 | — | — | 547.3 | — |
| 4 | Lotus seed | — | 244.9 | — | — | — | 224.9 |
| 11 | Ganoderma, red jujube and longan | 1:1:1 | 395.8 | 37.1*1/3 = 12.4 | 603*1/3 = 201 | 547.3*1/3 = 182.4 | — |

Note:
Dry weight of Test sample 11, 395.8 mg ≒ Estimated dry weight of Ganoderma extract contained therein, 12.4 mg + Estimated dry weight of red jujube extract contained therein, 201 mg + Estimated dry weight of longan extract contained therein, 182.4 mg

TABLE 4

Illustrative estimation method for dry weights of extracts of the
respective herbal materials contained in a test sample with four-ingredient compound

| Sample number | Herbal materials containted in preparation raw material | Weight ratio of Herbal materials contained in 1 g preparation raw material | Dry weight of sample | Estimated dry weight of respective extracts contained in the test sample (mg) | | | |
|---|---|---|---|---|---|---|---|
| | | | | Ganoderma extract | Red jujube extract | Longan extract | Lotus seed extract |
| 1 | Ganoderma | — | 37.1 | 37.1 | — | — | — |
| 2 | Red jujube | — | 603 | — | 603 | — | — |
| 3 | Longan | — | 547.3 | — | — | 547.3 | — |
| 4 | Lotus seed | — | 224.9 | — | — | — | 224.9 |
| 15A | Ganoderma, red jujube, longan and lotus seed | 1:1:1:1 | 352.4 | 37.1*1/4 = 9.3 | 603*1/4 = 150.1 | 547.3*1/4 = 136.8 | 224.9*1/4 = 56.2 |

Note:
Dry weight of Test sample 15A, 352.4 mg ≒ Estimated dry weight of Ganoderma extract contained therein, 9.3 mg + Estimated dry weight of red jujube extract contained therein, 150.1 mg + Estimated dry weight of longan extract contained therein, 136.8 mg + Estimated dry weight of lotus seed extract contained therein, 56.2 mg

TABLE 5

Illustrative estimation method for dry weights of extracts of the
respective herbal materials contained in a test sample with four-ingredient compound

| Sample number | Herbal materials containted in preparation raw material | Weight ratio of Herbal materials contained in 1 g preparation raw material | Dry weight of sample | Estimated dry weight of respective extracts contained in the test sample (mg) | | | |
|---|---|---|---|---|---|---|---|
| | | | | Ganoderma extract | Red jujube extract | Longan extract | Lotus seed extract |
| 1 | Ganoderma | — | 37.1 | 37.1 | — | — | — |
| 2 | Red jujube | — | 603 | — | 603 | — | — |
| 3 | Longan | — | 547.3 | — | — | 547.3 | — |
| 4 | Lotus seed | — | 244.9 | — | — | — | 224.9 |
| 15B | Ganoderma, red jujube, longan and lotus seed | 3:1:1:1 | 247.8 | 37.1*3/6 = 18.6 | 603*1/6 = 100.5 | 547.3*1/6 = 91.2 | 224.9*1/6 = 37.5 |

Note:
Dry weight of Test sample 15B, 247.8 mg ≒ Estimated dry weight of Ganoderma extract contained therein, 18.6 mg + Estimated dry weight of red jujube extract contained therein, 100.5 mg + Estimated dry weight of longan extract contained therein, 91.2 mg + Estimated dry weight of lotus seed extract contained therein, 37.5 mg Example 2

A. Methods

The 16 test samples prepared above were subjected to a cell lethal concentration test.

The cell lethal concentration test for the test samples were performed via the human colon adenocarcinoma cell Caco-2.

The cells were divided into a negative control (NC) and 16 experimental groups in which different test samples were used. For the negative control group, untreated cells were used, and for each experimental group, the test sample was diluted from the highest concentration of 200 µg/mL to each test concentration by a 2-fold dilution method (first, the test sample was prepared at a concentration of 100 mg/mL with ddH$_2$O, diluted with cell culture medium to a concentration of 200 µg/mL, and then diluted to each test concentration), and the test samples at different concentrations were respectively co-cultured with human colon adenocarcinoma cells Caco-2 in a 96-well culture plate for 48 hours.

After that, 0.5 mg/mL MTT was added to the negative control group and each experimental group and cultured for 4 hours, and then the medium was removed, the Formazan blue-violet crystal was dissolved by DMSO, and the absorbance at 570 nm was measured.

According to the formula shown below, the cell survival rate was evaluated.

Cell survival rate=(Absorbance at 570 nm for the experimental group/Absorbance at 570 nm for the negative control group (NC))×100%.

B. Results

Figure 1P:
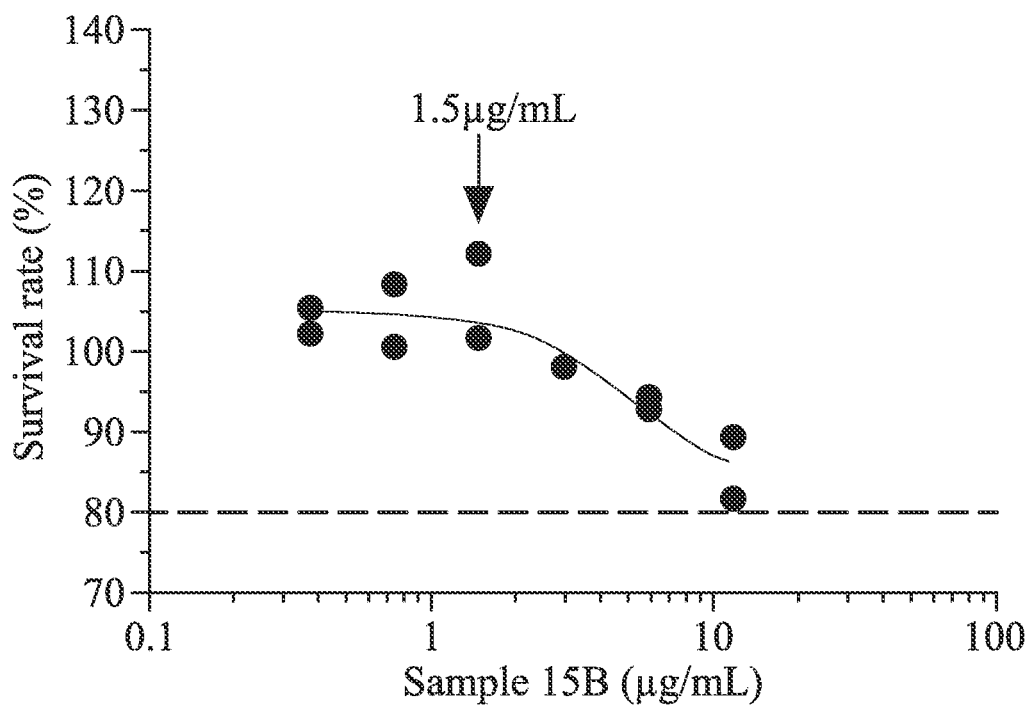

The results are shown in FIGS. 1A to 1P.

Based on FIG. 1A to FIG. 1P, the highest concentration for each sample that can be used without cell death as shown in Table 6 can be known.

TABLE 6

The highest concentration for each sample that can be used without cell death

| Sample number | Herbal materials contained in preparation raw material | Weight ratio of herbal materials contained in preparation raw material | Highest concentration that can be used without cell death (µg/mL) |
|---|---|---|---|
| 2 | Red jujube | — | 100 |
| 3 | Longan | — | 100 |
| 4 | Lotus seed | — | 100 |
| 8 | red jujube and longan | 1:1 | 100 |
| 10 | Longan and lotus seed | 1:1 | 100 |
| 9 | Red jujube and lotus seed | 1:1 | 25 |

TABLE 6-continued

The highest concentration for each sample that can be used without cell death

| Sample number | Herbal materials contained in preparation raw material | Weight ratio of herbal materials contained in preparation raw material | Highest concentration that can be used without cell death (μg/mL) |
|---|---|---|---|
| 14 | Red jujube, longan and lotus seed | 1:1:1 | 25 |
| 11 | Ganoderma, red jujube and longan | 1:1:1 | 6 |
| 13 | Ganoderma, longan and lotus seed | 1:1:1 | 6 |
| 1 | Ganoderma | | 3 |
| 6 | Ganoderma and longan | 1:1 | 3 |
| 12 | Ganoderma, red jujube and lotus seed | 1:1:1 | 3 |
| 15A | Ganoderma, red jujube, longan and lotus seed | 1:1:1:1 | 3 |
| 15B | Ganoderma, red jujube, longan and lotus seed | 3:1:1:1 | 1.5 |
| 5 | Ganoderma and red jujube | 1:1 | 0.75 |
| 7 | Ganoderma and lotus seed | 1:1 | 0.75 |

Example 3: Effect of Single-Ingredient Extract on Intestinal Epithelial Cell Permeability A. Methods The intestinal permeability system constructed by human intestinal epithelial cells was used to evaluate the effects of the respective extracts obtained in Example 1 on intestinal permeability (Pham V T, Seifert N, Richard N, et al. The effects of fermentation products of prebiotic fibres on gut barrier and immune functions in vitro [published correction appears in PeerJ. 2018 Aug. 17; 6:. Steinert, Robert [corrected to Steinert, Robert E]]. PeerJ. 2018; 6:e5288. Published 2018 Aug. 10. doi: 10.7717/peerj.5288). The detailed implementation steps are as follows.

After culturing the human colon adenocarcinoma cell Caco-2 on a transwell culture plate for 21 days, the cells were divided into a negative control (NC), a positive control (PC) and 4 experimental groups to perform an in vitro leaky gut assay. The negative control group was untreated cells. The positive control group was cells treated with 50 μM berberine chloride (Valenzano M C, DiGuilio K, Mercado J, Teter M, To J, Ferraro B, et al. (2015) Remodeling of Tight Junctions and Enhancement of Barrier Integrity of the CACO-2 Intestinal Epithelial Cell Layer by Micronutrients. PLOS ONE 10(7): e0133926.).

The 4 experimental groups were cells respectively treated with Sample 1, Sample 2, Sample 3, and Sample 4 at a concentration that does not cause cell death (Sample 1: 3 μg/mL; Sample 2: 100 μg/mL; Sample 3: 100 μg/mL; Sample 4: 100 μg/mL) (first, the sample was prepared at a concentration of 100 mg/mL with ddH$_2$O, diluted with cell culture medium to a concentration of 200 μg/mL, and then diluted to each test concentration).

The cells of each group were cultured for 48 hours after the treatment mentioned above, and then the cells were induced with 350 μg/mL rhamnolipids to induce cell permeabilization.

Next, FITC-dextran 4 (FD4) fluorescent dye was added to the inner plate of the transwell culture plate, and after reacting for 4 hours, the liquid in the lower well of the culture plate was aspirated to detect fluorescence intensity thereof (wavelength of excitation light: 485 nm; wavelength of emission light: 538 nm).

According to the formula shown below, the permeability of intestinal cells was evaluated by the fluorescence intensity of the liquid obtained from the lower well.

$$FD4 \text{ leakage rate} = (FD4 \text{ fluorescence value of the test sample}/FD4 \text{ fluorescence value of the negative control group (NC)}) \times 100\%.$$

B. Results

Figure 2:
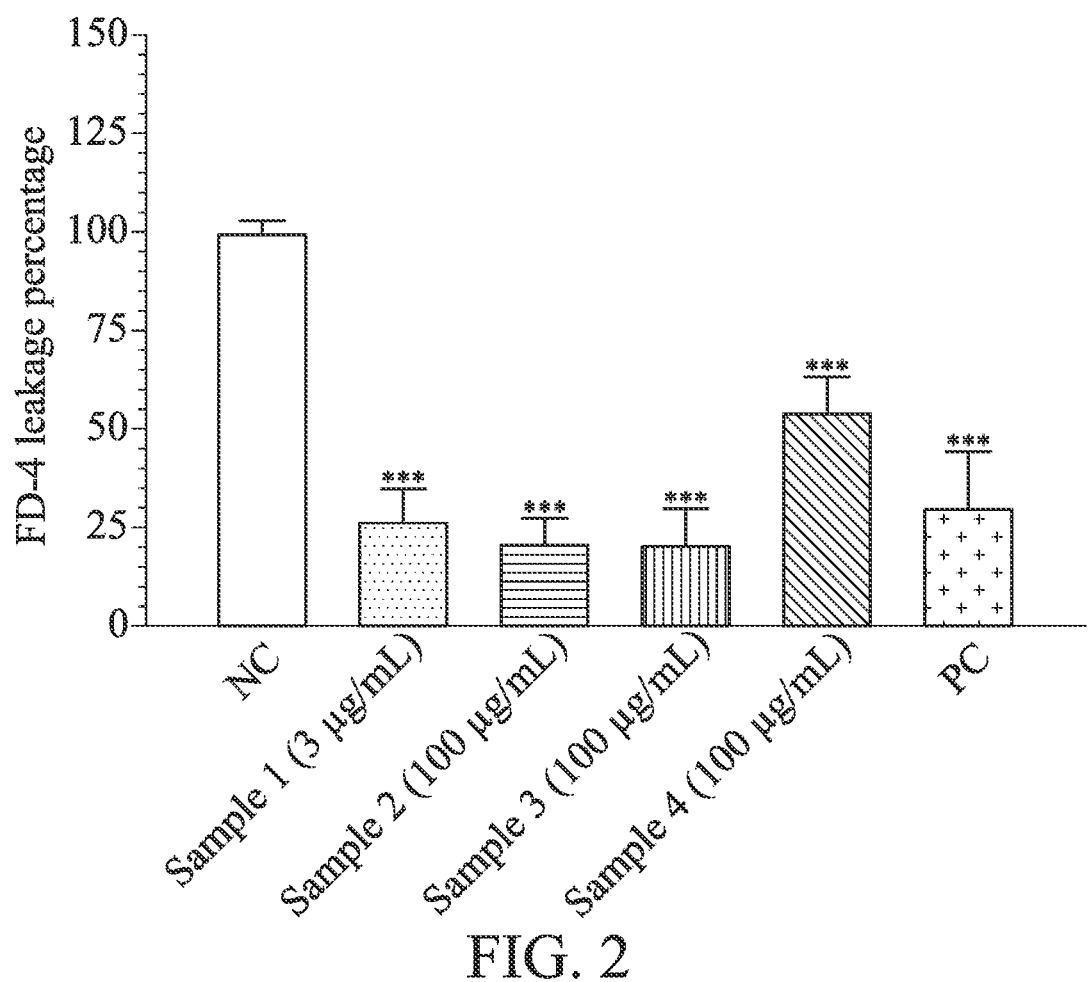
FIG. 2 shows the results of the intestinal epithelial cell permeability test of the single-ingredient extract. ***: $p<0.001$, compared to the negative control group. The data are shown as mean±standard deviation (Mean±SD) (n=3). The statistical method is one-way ANOVA.
Figure 4A:
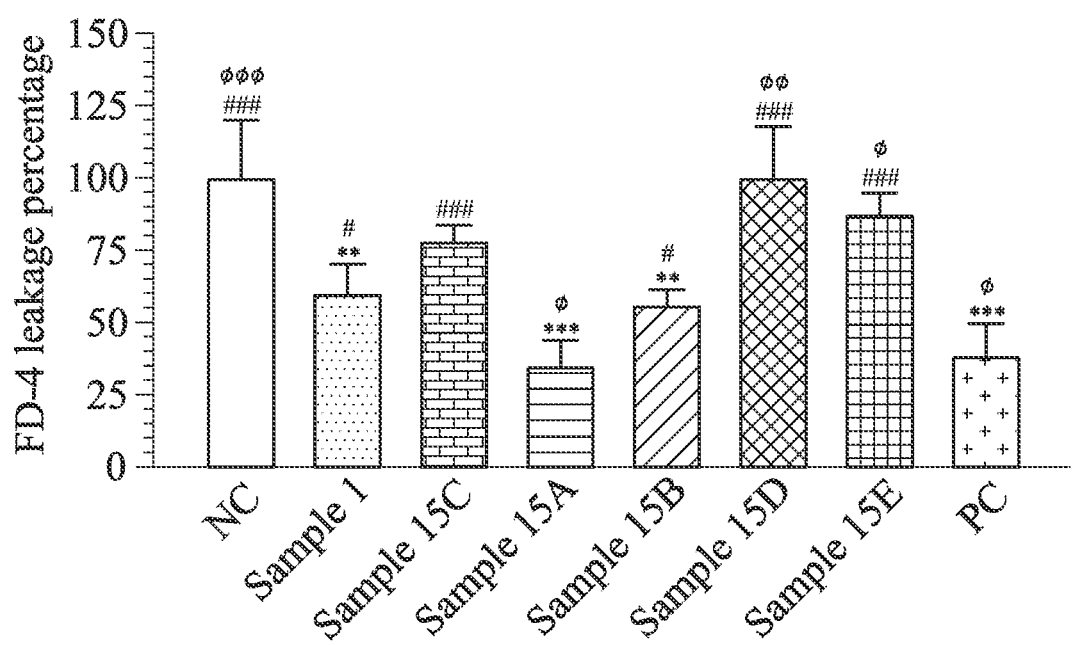
Figure 4B:
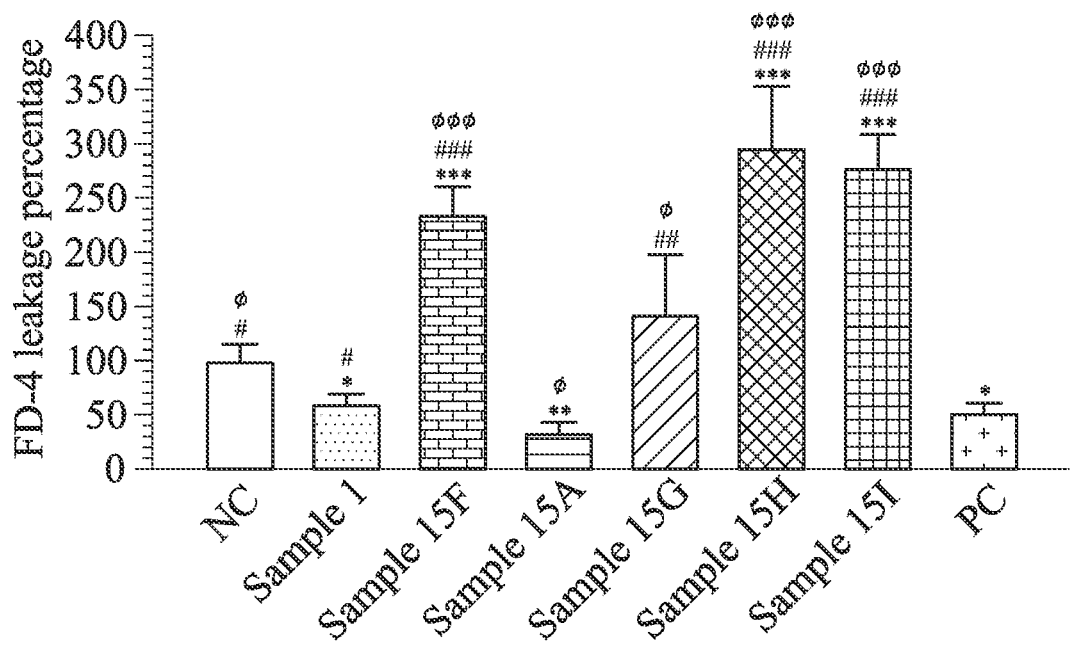
Figure 4C:
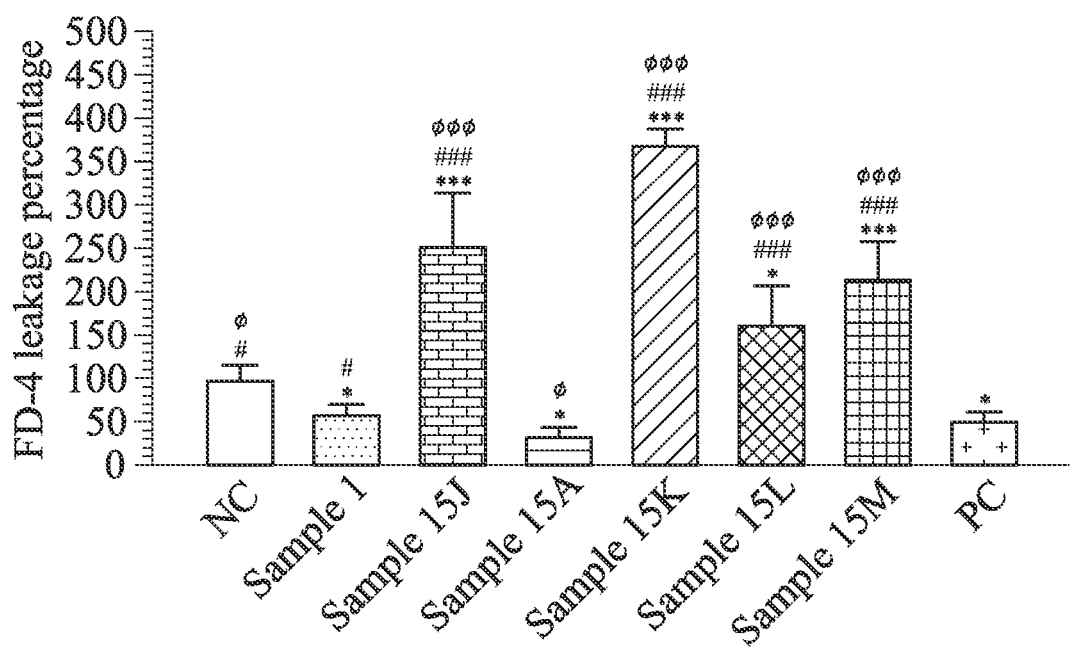

The results are shown in FIG. 2.

FIG. 2 shows that Sample 1 (*Ganoderma* extract), Sample 2 (red jujube extract), Sample 3 (longan extract) and Sample 4 (lotus seed extract) all are capable of significantly reducing the FD4 leakage rate, and this represents that Sample 1 to Sample 4 all have the activity of inhibiting intestinal permeability.

Example 4: Effect of Compound Extract on Intestinal Epithelial Cell Permeability A. Methods The intestinal permeability system constructed by human intestinal epithelial cells was used to evaluate the effects of the respective extracts obtained in Example 1 on intestinal permeability. The detailed implementation steps are as follows.

After culturing the human colon adenocarcinoma cell Caco-2 on a transwell culture plate for 21 days, the cells were divided into a negative control (NC), a positive control (PC) and 9 experimental groups to perform an in vitro leaky gut assay. The negative control group was untreated cells. The positive control group was cells treated with 50 μM berberine chloride. The 9 experimental groups were cells respectively treated with 1.5 μg/mL of Sample 1, Sample 2, Sample 3, Sample 4, Sample 6, Sample 9, Sample 11, Sample 12 and Sample 15A.

The cells of each group were cultured for 48 hours after the treatment mentioned above, and then the cells were induced with 350 μg/mL rhamnolipids to induce cell permeabilization.

Next, FITC-dextran 4 (FD4) fluorescent dye was added to the inner plate of the transwell culture plate, and after reacting for 4 hours, the liquid in the lower well of the culture plate was aspirated to detect fluorescence intensity thereof (wavelength of excitation light: 485 nm; wavelength of emission light: 538 nm).

According to the formula shown below, the permeability of intestinal cells was evaluated by the fluorescence intensity of the liquid obtained from the lower well.

$$FD4 \text{ leakage rate} = (FD4 \text{ fluorescence value of the test sample}/FD4 \text{ fluorescence value of the negative control group (NC)}) \times 100\%.$$

B. Results

The results are shown in FIG. 3.

FIG. 3 shows that when the concentration of Sample 2 (red jujube extract), Sample 3 (longan extract) and Sample 4 (lotus seed extract) is reduced from the 100 μg/mL used in Example 3 to 1.5 μg/mL, Sample 2, Sample 3 and Sample 4 do not significantly reduce the FD4 leakage rate, while only Sample 1 is capable of significantly reducing FD4 leakage rate.

Furthermore, FIG. 3 also shows that for different compound extracts, only Sample 12 (*Ganoderma* extract+red jujube extract+lotus seed extract (the weight ratio of the respective herbal raw materials used to obtain the respective extracts is 1:1:1)) and Sample 15A (*Ganoderma* extract+red jujube extract+lotus seed extract+lotus seed extract (the weight ratio of the respective herbal raw materials used to obtain the respective extracts is 1:1:1:1)) are capable of significantly reducing the FD4 leakage rate. At the same concentration (1.5 μg/mL), compared to Sample 1 and Sample 12, Sample 15A can more significantly inhibit the FD4 leakage rate, and this represents that Sample 15A has a better activity in inhibition of intestinal permeability.

Example 5: Effects of Four-Ingredient Compounds in Different Proportions on Intestinal Epithelial Cell Permeability A. Methods The intestinal permeability system constructed by human intestinal epithelial cells was used to evaluate the effects of the respective extracts obtained in Example 1 on intestinal permeability. The detailed implementation steps are as follows.

After culturing the human colon adenocarcinoma cell Caco-2 on a transwell culture plate for 21 days, the cells were divided into a negative control (NC), a positive control (PC) and 6 experimental groups to perform an in vitro leaky gut assay.

In this experiment, the experiment was conducted in 4 batches. In each batch, the negative control groups were all untreated cells, and the positive control groups were all cells treated with 50 μM berberine chloride.

In the first batch, the 6 experimental groups were cells treated with 1.5 μg/mL of Sample 1, Sample 15A, Sample 15B, Sample 15C, Sample 15D, and Sample 15E, respectively.

In the second batch, the 6 experimental groups were cells treated with 1.5 μg/mL of Sample 1, Sample 15A, Sample 15F, Sample 15G, Sample 15H, and Sample 15I, respectively.

In the third batch, the 6 experimental groups were cells treated with 1.5 μg/mL of Sample 1, Sample 15A, Sample 15J, Sample 15K, Sample 15L, and Sample 15M, respectively.

In the fourth batch, the 6 experimental groups were cells treated with 1.5 μg/mL of Sample 1, Sample 15A, Sample 15N, Sample 15O, Sample 15P, and Sample 15Q.

The cells of each group were cultured for 48 hours after the treatment mentioned above, and then the cells were induced with 350 μg/mL rhamnolipids to induce cell permeabilization.

Next, FITC-dextran 4 (FD4) fluorescent dye was added to the inner plate of the transwell culture plate, and after reacting for 4 hours, the liquid in the lower well of the culture plate was aspirated to detect fluorescence intensity thereof (wavelength of excitation light: 485 nm; wavelength of emission light: 538 nm).

According to the formula shown below, the permeability of intestinal cells was evaluated by the fluorescence intensity of the liquid obtained from the lower well.

FD4 leakage rate=(FD4 fluorescence value of the test sample/FD4 fluorescence value of the negative control group (NC))×100%.

B. Results

The results of the first batch of experiments, the second batch of experiments, the third batch of experiments, and the fourth batch of experiments are shown in FIG. 4A, FIG. 4B, FIG. 4C, and FIG. 4D, respectively.

According to FIG. 4A, FIG. 4B, FIG. 4C, and FIG. 4D, it can be seen that Sample 15A (*Ganoderma* extract+red jujube extract+lotus seed extract+lotus seed extract (the weight ratio of the respective herbal raw materials used to obtain the respective extracts is 1:1:1:1)) and Sample 15B (*Ganoderma* extract+red jujube extract+lotus seed extract+ lotus seed extract (the weight ratio of the respective herbal raw materials used to obtain the respective extracts is 3:1:1:1)) have better activities in inhibition of intestinal permeability, wherein Sample 15A can inhibit intestinal permeability more significantly than Sample 15B.

Example 6: Effects of Four-Ingredient Compound Extract on Intestinal Epithelial Cell Permeability The intestinal permeability system constructed by human intestinal epithelial cells was used to evaluate the effect of Sample 15B (*Ganoderma* extract+red jujube extract+lotus seed extract+lotus seed extract (the weight ratio of the respective herbal raw materials used to obtain the respective extracts is 3:1:1:1)) obtained in Example 1 on intestinal permeability. The detailed implementation steps are as follows.

After culturing the human colon adenocarcinoma cell Caco-2 on a transwell culture plate for 21 days, the cells were divided into two negative control (NC) groups, two positive control (PC) groups and 6 experimental groups to perform an in vitro leaky gut assay The two negative control groups were untreated cells. The two positive control groups were cells treated with 50 μM berberine chloride. The 6 experimental groups were cells respectively treated with Sample 15B at concentrations of 0.3 μg/mL, 0.3 μg/mL, 0.6 μg/mL, 0.6 μg/mL, 1.5 μg/mL, and 1.5 μg/mL, respectively.

The cells in each group were cultured for 48 hours after the above treatment, and then the cells in half of the groups in the experiment (including a negative control group, a positive control group and experimental groups treated with 3 concentrations of Sample 15B) were treated at 350 g/mL rhamnolipids to induce cell permeabilization while the cells in the other half of the groups in the experiment were not treated with rhamnolipid.

Next, FITC-dextran 4 (FD4) fluorescent dye was added to the inner plate of the transwell culture plate, and after reacting for 4 hours, the liquid in the lower well of the culture plate was aspirated to detect fluorescence intensity thereof (wavelength of excitation light: 485 nm; wavelength of emission light: 538 nm).

According to the formula shown below, the permeability of intestinal cells was evaluated by the fluorescence intensity of the liquid obtained from the lower well.

FD4 leakage rate=(FD4 fluorescence value of the test sample/FD4 fluorescence value of the negative control group (NC))×100%.

B. Results

Figure 5:
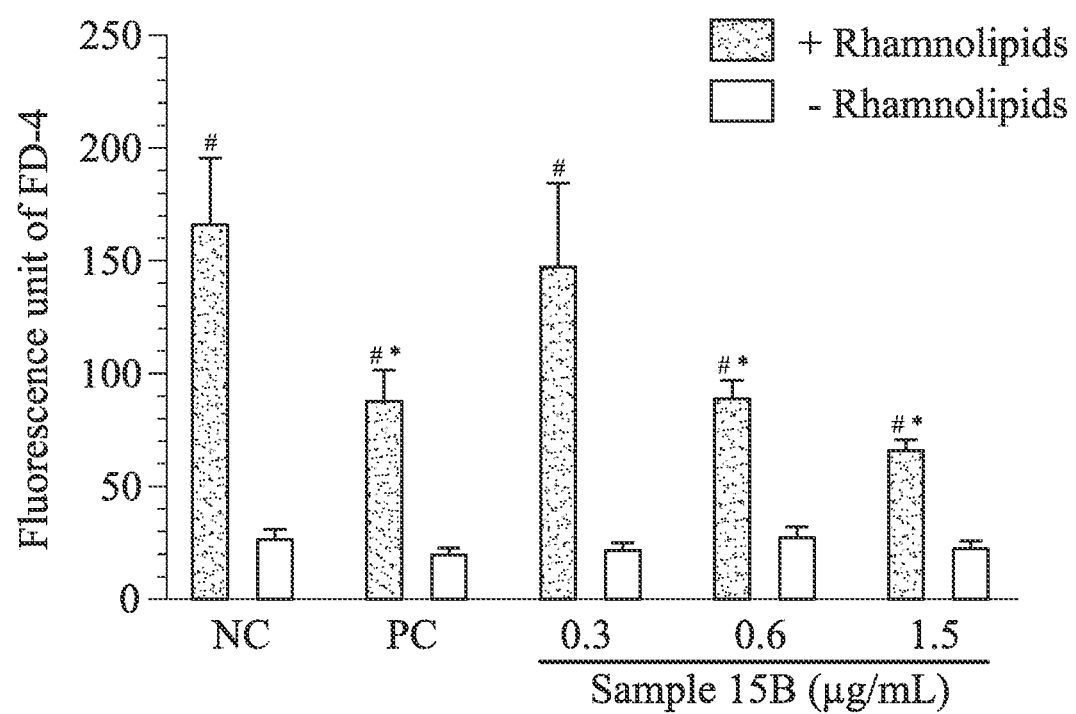
FIG. 5 shows the results of the intestinal epithelial cell permeability test of Sample 15B at different concentrations. Compared to the negative control group treated with rhamnose: *: $p<0.05$; in the positive control groups and each experimental group, the group treated with rhamnolipids compared to the group without rhamnose treatment: #: $p<0.05$. The data are shown as mean±standard deviation (n=3). The statistical method is one-way ANOVA.

The results are shown in FIG. 5. The cells in the groups not treated with rhamnolipid showed no obvious fluorescence intensity. In the negative control groups, compared to the group not induced with rhamnolipid, the fluorescence intensity of the group induced with rhamnolipid was significantly increased, and in the groups induced with rhamnolipid, Sample 15B (*Ganoderma* extract+red jujube extract+lotus seed extract+lotus seed extract (the weight ratio of the respective herbal raw materials used to obtain the respective extracts is 3:1:1:1)) at concentrations of 0.6 μg/mL and 1.5 μg/mL could significantly reduce the fluorescence intensity, and this represents that it has an activity in inhibition of intestinal permeability.

Example 7: Effect of Four-Ingredient Compound Extract on Gene Expression Levels of Adherent and Tight Junctions Proteins of Intestinal Epithelial Cells A. Methods The cells in the negative control group, the positive control group and the experimental group (treated with Sample 15B at a concentration of 1.5 µg/mL) in the groups induced by rhamnolipid in Example 6 were collected.

Total ribonucleic acid (total RNA) of cells was isolated by Total RNA Purification Kit (GeneMark, Taichung, Taiwan). Using Maxima First Strand cDNA Synthesis Kit (Thermo Fisher Scientific), according to the manufacturer's operating procedures, the obtained total ribonucleic acid subjected to a reverse transcription polymerase chain reaction to reverse-transcript messenger ribonucleic acid (mRNA) into cDNA.

Next, the cDNA samples were subjected to a real-time quantitative polymerase chain reaction to determine the expression levels of CLDN3, OCLN and TJP1 mRNA. The difference in gene expression was calculated by a relative quantitative data analysis through $2^{-(\Delta\Delta CT)}$, and glyceraldehyde 3-phosphate dehydrogenase (GAPDH) was used as the reference gene. The primers used for the respective genes are shown in Table 7.

TABLE 7

Primers used for respective genes

| Gene | Forward primer (5'-3') | Reverse primer (5'-3') |
|---|---|---|
| CLDN3 | ATCGTGTGCTGCGCGTT (SEQ ID NO. 1) | GGCCCTCCCAGATGTTCTG (SEQ ID NO. 2) |
| OCLN | GTCCAATATTTTGTGGG ACAAGG (SEQ ID NO. 3) | GGCACGTCCTGTGTGCCT (SEQ ID NO. 4) |
| TJP1 | AGAAGGATGTTTATCGT CGCATT (SEQ ID NO. 5) | CCAAGAGCCCAGTTTTCCAT (SEQ ID NO. 6) |
| GAPDH | CAAGGTCATCCATGACA ACTTTG (SEQ ID NO. 7) | GTCCACCACCCTGTTGCTGT AG (SEQ ID NO. 8) |

B. Results

Figure 6A:
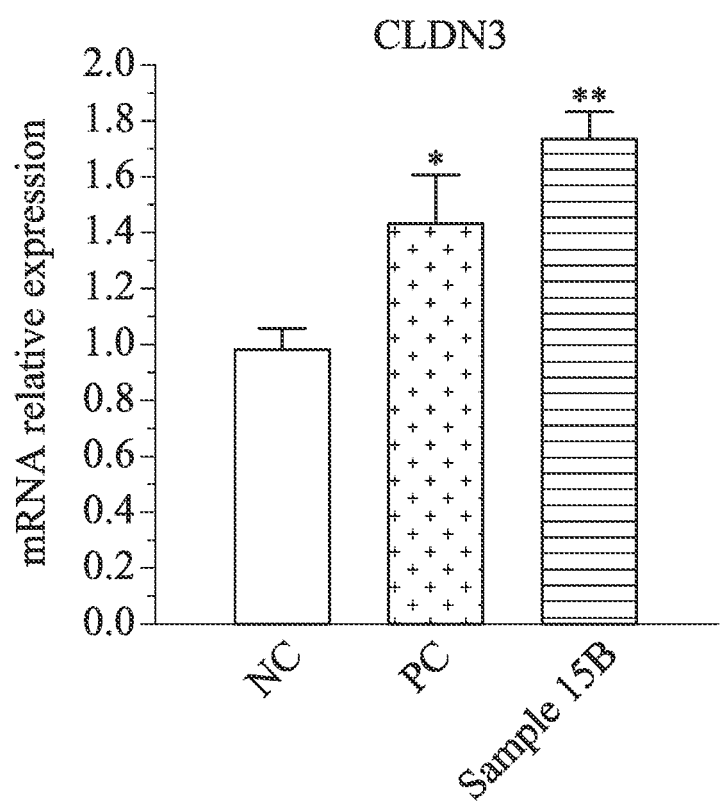
FIGS. 6A to 6C respectively show the effect of Sample 15B on the expression of CLDN3, OCLN and TJP1 genes. The negative control group is untreated cells, and the positive control group is treated with berberine chloride (BBC) at 50 μM (18.6 μg/mL). Compared to the negative control group: *: $p<0.05$; **: $p<0.01$; ns: not significant. The data are shown as mean±standard deviation (n=3). The statistical method is one-way ANOVA.
Figure 6B:
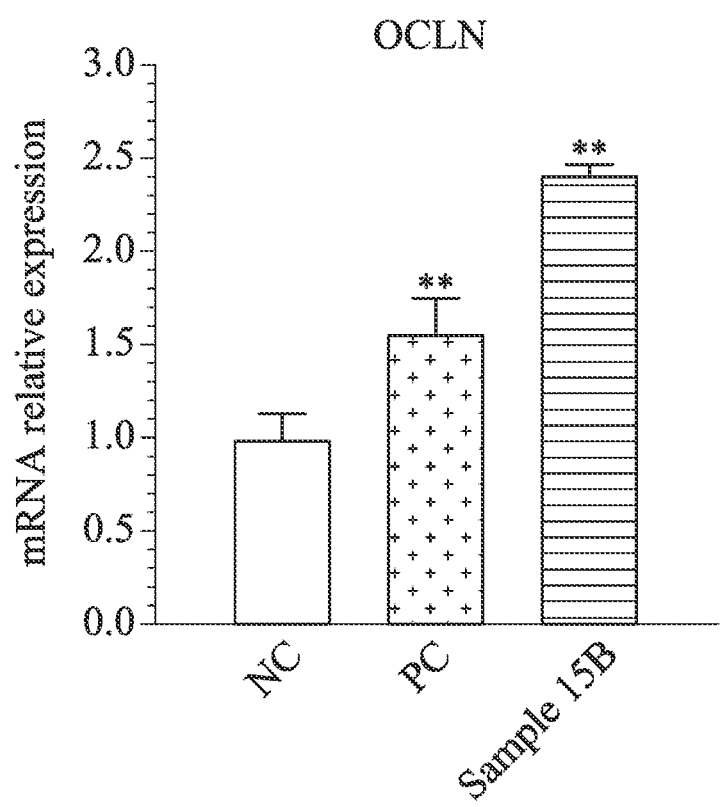
Figure 6C:
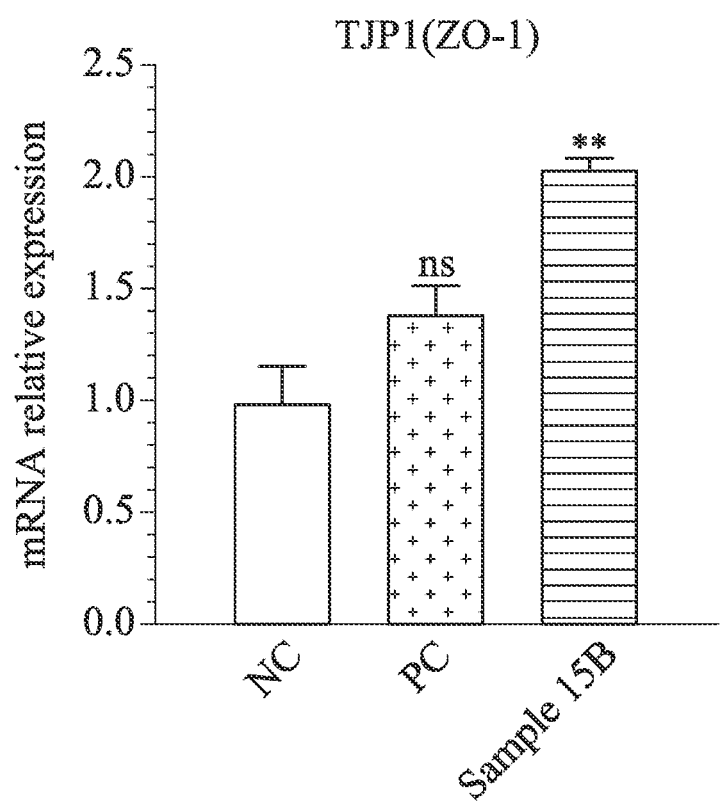

The results are shown in FIGS. 6A, 6B and 6C. The results showed that compared to the negative control group, the positive control group and the experimental group can significantly increase the expression levels of CLDN3, OCLN and TJP1 genes.

Example 8: Effect of Four-Ingredient Compound Extract on Dextran Sulfate Sodium Salt (DSS) Induced Abnormal Intestinal Permeability in Animals A. Methods The animals used in this experiment were 5-6 week old C57BL/6 male mice (purchased from the National Laboratory Animal Center).

The experiment was performed by an animal model of dextran sulfate sodium salt (DSS) induced abnormal intestinal permeability (Laroui H, Ingersoll S A, Liu H C, Baker M T, Ayyadurai S, et al. (2012) Dextran Sodium Sulfate (DSS) Induces Colitis in Mice by Forming Nano-Lipocomplexes with Medium-Chain-Length Fatty Acids in the Colon. PLOS ONE 7(3): e32084. doi:10.1371/journal.pone.0032084).

The mice were divided into an untreated group (Naive), a negative control group (vehicle: water), a positive control group (5-aminosalicylic acid (5-ASA)) and 3 experiments groups (Sample 15B (*Ganoderma* extract+red jujube extract+lotus seed extract+lotus seed extract (the weight ratio of the respective herbal raw materials used to obtain the respective extracts is 3:1:1:1))). The mice in the untreated group were not treated in any way. The mice in the negative control group were given drinking water containing 0.5% (v/v) dextran sodium sulfate (MP Biomedicals) to induce abnormal intestinal permeability; the mice in the positive control group were given 0.5% (v/v) dextran sulfate sodium salt and 200 µM 5-aminosalicylic acid. The mice in the 3 experimental groups were given 0.5% (v/v) dextran sulfate sodium salt and 100 mg/kg Sample 15B, 0.5% (v/v) dextran sulfate sodium salt and 200 mg/kg Sample 15B, and 0.5% (v/v) dextran sulfate sodium salt and 400 mg/kg Sample 15B, respectively.

The experiment lasted for 14 days. On the day of the end of the experiment, after fasting the mice for 3-4 hours, the mice were given FITC-dextran (FD4, Sigma) at 500 mg/kg. After 2 hours, the mice were sacrificed, their blood was collected, and the serum was separated.

The FITC-dextran content in mouse serum was measured with a multifunctional microplate spectrometer (Molecular Device, FlexStation® 3) as an indicator of intestinal permeability.

B. Results

Figure 7:
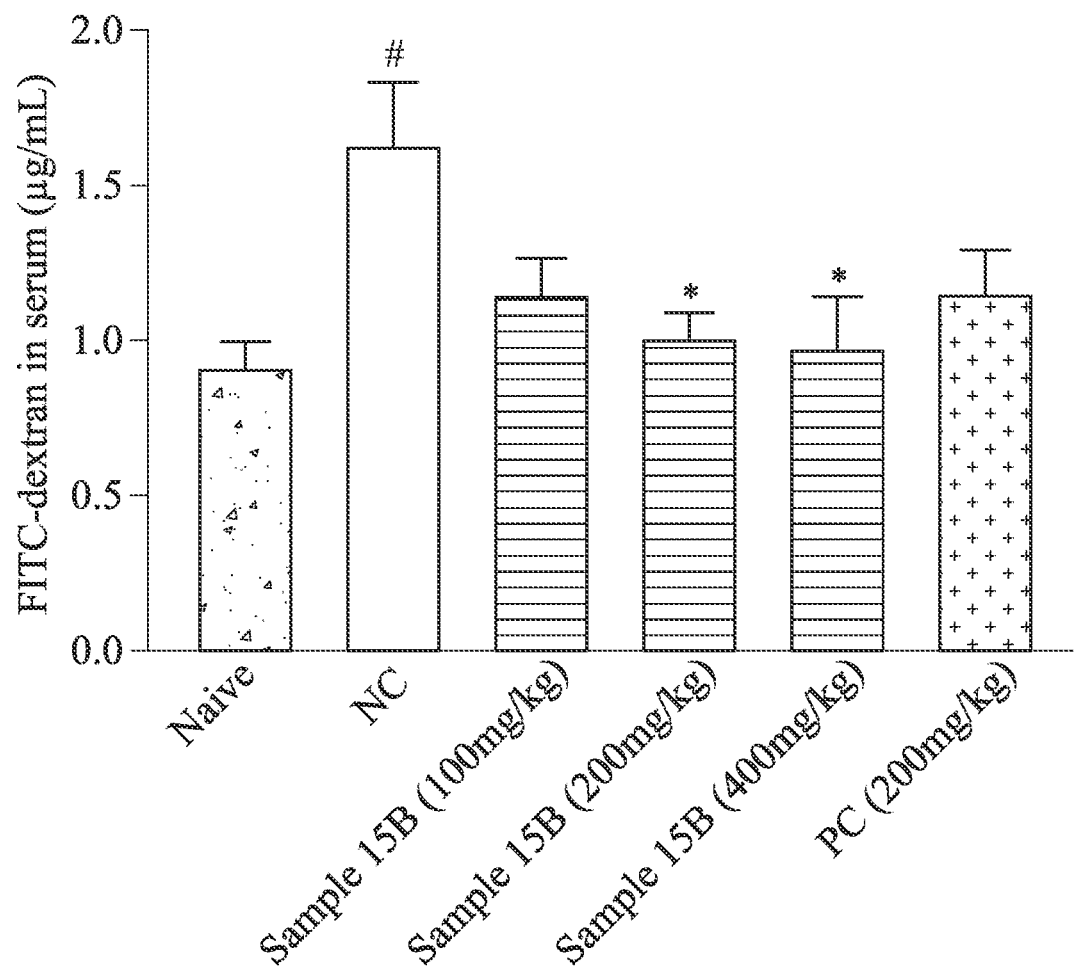
FIG. 7 shows the effect of Sample 15B on the intestinal permeability of DSS-induced mice. Compared to the untreated group: #: $p<0.05$. Compared to the negative control group: *: $p<0.05$. The data are shown as mean±standard deviation (n=3-4). The statistical method is t test.

FIG. 7 shows that compared to the untreated group, the concentration of FITC-FITC-dextran in the serum of the negative control group treated with 0.5% (v/v) DSS significantly increases, and this shows that 0.5% (v/v) dextran sulfate sodium salt can induce increase of intestinal permeability in mice. Moreover, compared to the negative control group, the positive control group and the experimental groups can reduce the serum FITC-dextran concentration, and this shows that Sample 15B (*Ganoderma* extract+red jujube extract+lotus seed extract+lotus seed extract (the weight ratio of the respective herbal raw materials used to obtain the respective extracts is 3:1:1:1)) can ameliorate the increase in intestinal permeability induced by dextran sulfate sodium salt.

Example 9: The Effect of Four-Ingredient Compound Extract on Circadian Disruption Animal Model A. Methods The animals used in this experiment were 8-week-old C57BL/6 male mice (purchased from the National Laboratory Animal Center).

The mice were subjected to a surgical operation to load electrodes on the skull to record brain waves. After a 7-day recovery period, the mice were reared for 2 weeks under a normal light-dark cycle of 12 hours: 12 hours, and the 24-hour brainwave changes of the mice were recorded as the basic point.

Next, the mice were divided into an untreated group (Naive), a negative control group (vehicle), a positive control group (Diazepam) and an experimental group (Sample 15B (*Ganoderma* extract+red jujube extract+lotus seed extract+lotus seed extract (the weight ratio of the respective herbal raw materials used to obtain the respective extracts is 3:1:1:1)). Mice in the untreated group were kept in a normal light-dark cycle for two weeks (the light-dark cycle was 12 hours: 12 hours). The mice in the negative control group, the positive control group and the experimental group were reared for 7 days under the condition of a light-dark cycle of 7 hours: 7 hours to induce insomnia in the mice through circadian disruption. During the feeding, the mice in the negative control group were given the same amount of sterile water, mice in the positive control group were given diazepam (2.5 mg/kg orally), and mice in the experimental group were given 200 mg/kg Sample 15B.

The 24-hour brainwave changes of mice were recorded on Day 4 after the circadian disruption to analyze sleep cycle parameters of the time proportions (%) of the rapid eye movement (REM) and non-rapid eye movement (NREM), etc.

B. Results

Figure 8:
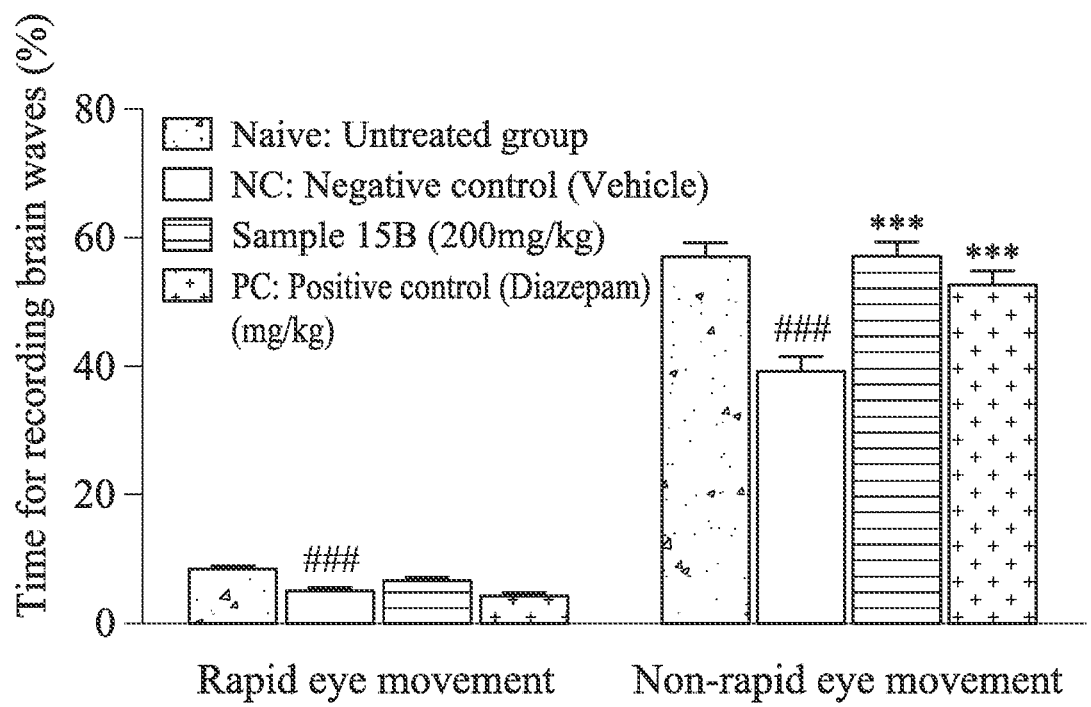
FIG. 8 shows the effect of Sample 15B on animals with circadian disruption. Compared to the untreated group: ###: $p<0.001$. Compared to the negative control group: *** $p<0.001$. The data are shown as mean±standard deviation (n=6). The statistical method is that the data is one-way ANOVA and Dunnett's test.

The results are shown in FIG. 8. The results show that compared to the untreated group, the time proportion of the rapid eye movement and the time proportion of the non-rapid eye movement of the negative control group are both significantly reduced, and this indicates that the circadian disruption can induce insomnia in mice. Moreover, compared to the negative control group, both the positive control group and the experimental group can significantly increase the time proportion of the non-rapid eye movement, and have the effect of alleviating insomnia in mice.

Example 10: Effect of Four-Ingredient Compound Extract on Amyloid β-induced Spatial Learning Disability of Animals A. Methods The effect of Sample 15B on learning and operating ability was evaluated by an animal model in which formation of amyloid-β plaque deposition in animal brains was induced by amyloid β (Kim, H Y, Lee, D K, Chung, B R, Kim, H V, Kim, Y. Intracerebroventricular Injection of Amyloid-β Peptides in Normal Mice to Acutely Induce Alzheimer-like Cognitive Deficits. J. Vis. Exp. (109), e53308, doi:10.3791/53308 (2016).). The experimental steps are described as follows:

The animals used in this experiment were Sprague-Dawley male rats (body weight 300-330 g, purchased from Lesco).

The rats were divided into a Sham group, a control group and an experimental group. The rats in the Sham group were injected with artificial cerebrospinal fluid, the rats in the control group were injected with 2.5 µL amyloid β peptide 1-40, and the rats in the experimental group were injected with 2.5 µL amyloid β peptide 1-40 and orally administered with Sample 15B (127 mg/kg/day) for 30 days, continuously.

Evaluation Tests of Locomotion and Exploratory Behavior were Conducted on Day 22 to Day 23 of the Experiment The Evaluation for locomotion and exploratory behavior are described as follows:

Evaluation tests of locomotion and exploratory behavior for rats were performed in an experiment box. The experiment box had a size of 40 cm in length, width and height. In addition, the experiment box had a stainless steel bottom plate, and the bottom plate had 16 holes with a diameter of 3 cm, which were arranged in a 4*4 matrix, and the distance between two adjacent holes was 4 cm, and the distance between the each side of the matrix and the hole was 7 cm. The movement of the rat was sensed and record by the sensors, TruScan Line E63-01HS and TruScan Sensor E63-22 (Coulbourn Instruments International Corporation), and analyzed with the analysis software, Coulbourn Instruments' The Habitest System. The measurement time for each rat was 15 minutes. The measurement included the time spent in the holes, the frequency of hole-poking and the exploratory activities.

A water maze test was performed on the Day 24 to Day 28 of the experiment.

The water maze test is described as follows:

A swimming pool was divided into four quadrants, and the safe platform was fixed on the fourth quadrant. The rats were placed in the swimming pool (the respective rats were placed in a different quadrant in each test) and trained twice a day for 2 minutes each time. If a rat found a safe platform within 2 minutes, after the rat was allowed to rest for 30 seconds, the rat was allowed to leave the swimming pool and rest for 30 seconds, and then the next training was proceeded. If the rat had not found a safe platform within 2 minutes, after the rat was placed on the safe platform and rest for 30 seconds, the rat was allowed to leave the swimming pool and rest for 30 seconds, and then the next training was proceeded; The rats were trained for a total of 4 days.

Afterwards, a spatial performance in Morris water maze test and a non-spatial performance in Morris water maze test were performed respectively. In the spatial performance in Morris water maze test, a reference point was established at the relative position to the safe platform, and then a rat was placed in the first quadrant, and the time required for the rat to reach the former safety platform in the swimming pool was recorded. In the non-spatial performance in Morris water maze test, the reference point was removed, and a rat was placed in the first quadrant, and the time required for the rat to reach the former safe platform in the swimming pool was recorded.

On the next day after the end of the behavioral tests, the hippocampus area and frontal cortex areas of the brains of all animals were taken out to perform AChE activity analysis and determine the protein content.

B. Results

Figure 9A:
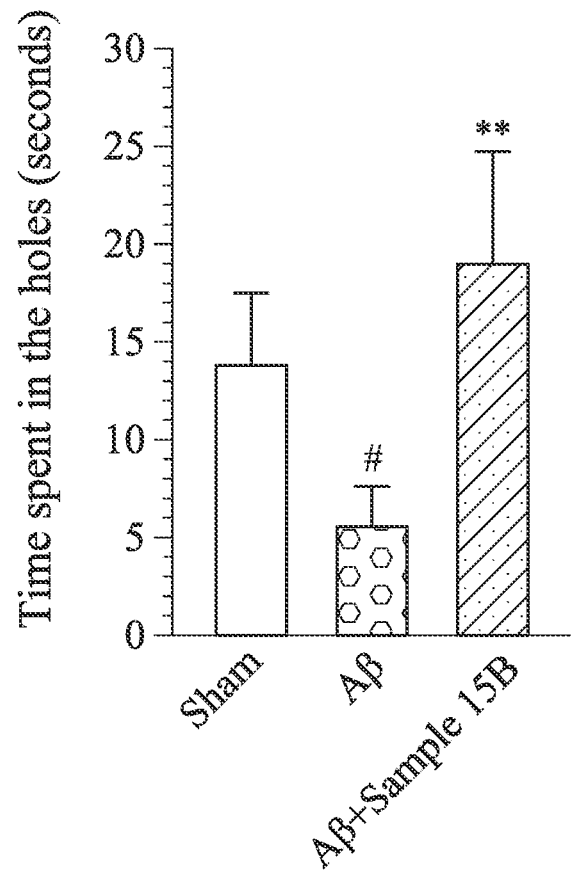
FIGS. 9A, 9B and 9C respectively show the effect of Sample 15B on the time spent in the holes, the frequency of hole-poking and the exploration activities of the rats in the evaluation test of locomotion and exploratory behavior. Compared to the Sham group: #: $p<0.05$, ##: $p<0.01$. Compared to the control group: *: $p<0.05$, **: $p<0.01$. The data are shown as mean±standard deviation (n=6). The statistical method is that the data is one-way ANOVA and Dunnett test.
Figure 9B:
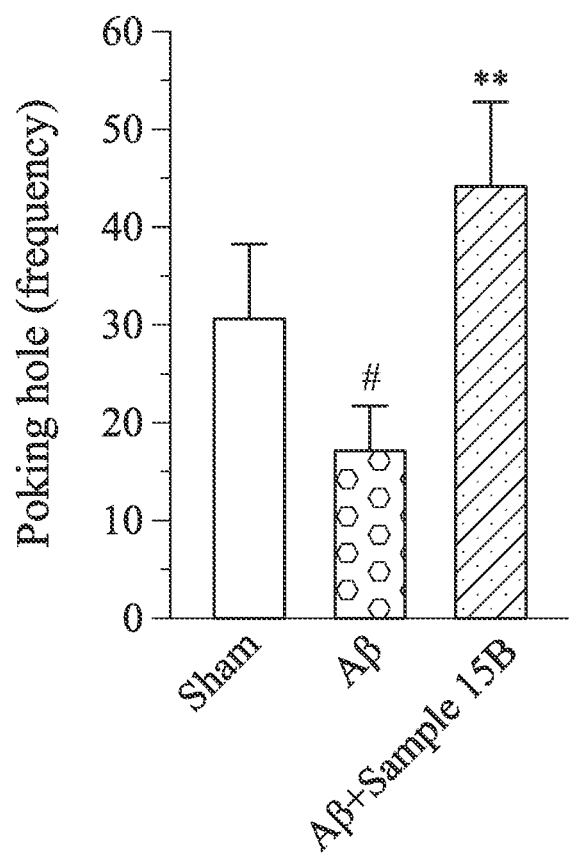
Figure 9C:
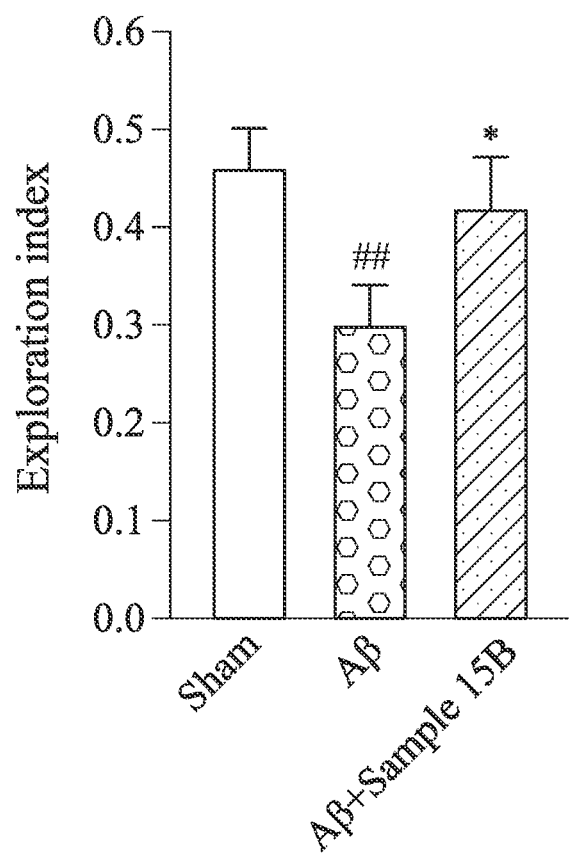

FIGS. 9A, 9B, and 9C show the results of the evaluation test of the locomotion and exploratory behavior of rats. The results shows that compared to the rats in the Sham group, the time spent in the holes, the number of times for hole-poking and the exploration activities for the rats in the control group given β-amyloid peptide 1-40 are reduced. However, the experimental group showed that Sample 15B can ameliorate the decrease for the time spent in the holes, the frequency of hole-poking and the exploration activities of the rats that caused by β-amyloid peptide 1-40, and can increase the time spent in the holes, the frequency of hole-poking and the exploration activities of the rats.

Figure 10:
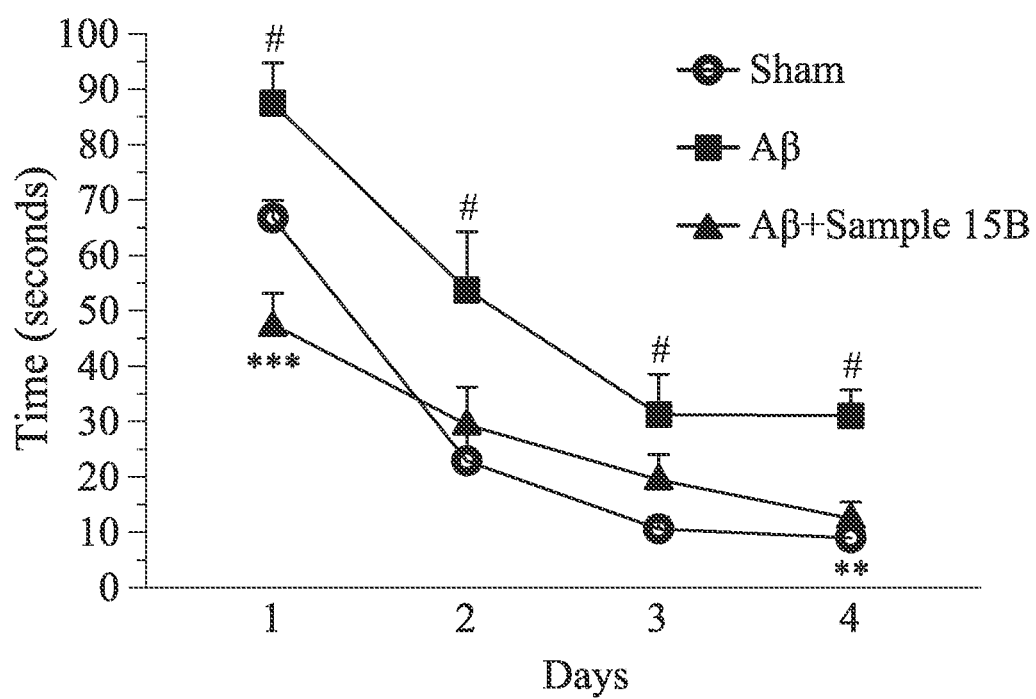
FIG. 10 shows the effect of Sample 15B on the time for rats to find a safe platform in the swimming pool in a spatial performance in Morris water maze test. Compared to the Sham group: #: $p<0.05$. Compared to the control group: : $p<0.01$; *: $p<0.001$. The data are shown as mean±standard deviation (n=6). The statistical method is that the data is one-way ANOVA and Dunnett test.
Figure 11:
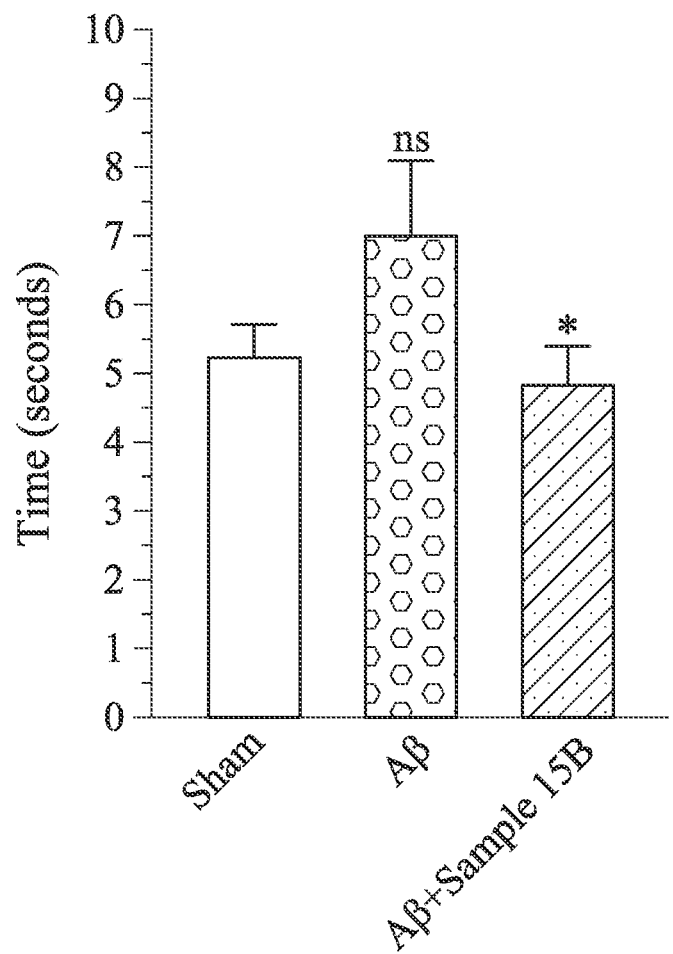
FIG. 11 shows the effect of Sample 15B on the time for rats to reach the safe platform in the swimming pool in a non-spatial performance in Morris water maze test. Compared to the Sham group: ###: $p<0.001$. Compared to the control group: *: $p<0.05$; ns: not significant. The data are shown as mean±standard deviation (n=6). The statistical method is that the data is one-way ANOVA and Dunnett test.

FIGS. 10 and 11 shows the results of the water maze test in rats.

FIG. 10 shows the time taken for rats to find a safe platform in the spatial performance in Morris water maze test. FIG. 10 shows that compared to the rats in the Sham group, the time for the rats in the control group given β-amyloid peptide 1-40 to reach the safety platform of the swimming pool was significantly longer. However, the experimental group showed that Sample 15B can ameliorate the spatial learning disabilities appears on Day 1 to Day 2, caused by β-amyloid peptide 1-40 in rats (i.e. shorten the time required to reach the safe platform).

FIG. 11 shows the time for rats to reach the safe platform in the non-spatial performance in Morris water maze test.

Compared to the rats in the Sham group, the rats in the control group given with β-amyloid peptide 1-40 spent significantly longer time to search for the area in which the safe platform placed. However, the experimental group shows that Sample 15B can ameliorate the reference memory difficulties caused by β-amyloid peptide 1-40 in rats (i.e., shorten the time to search for the area in which the safe platform placed in the swimming pool).

Figure 12A:
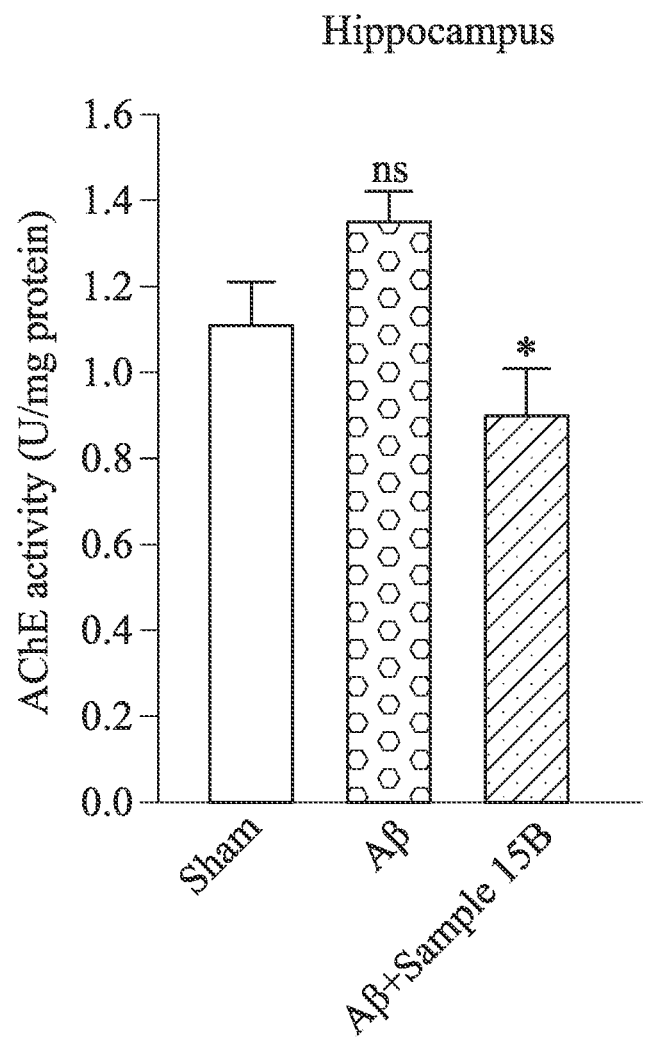
FIGS. 12A and 12B respectively show the effect of Sample 15B on the AChE activity in the hippocampus area and frontal cortex area of rats in the animal model of β-amyloid-induced learning impairment. Compared to the Sham group: #: $p<0.05$, ###: $p<0.001$. Compared to the control group: : $p<0.01$; *: $p<0.001$; ns: no significant. The data is that statistical method is that the data is one-way ANOVA and Dunnett test.
Figure 12B:
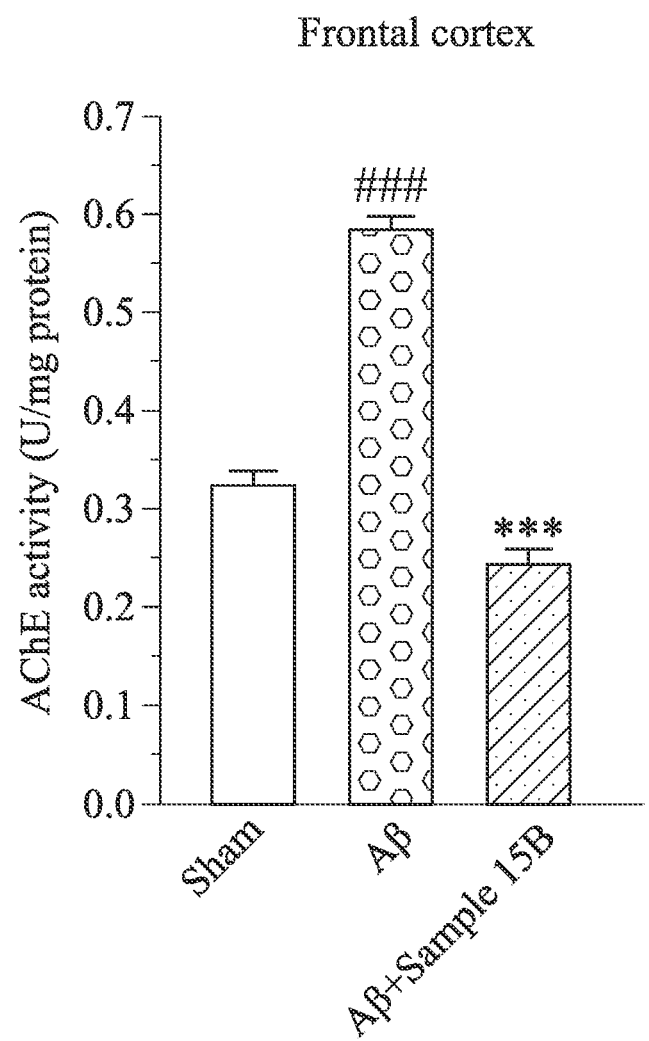

FIGS. 12A and 12B respectively show the AChE activity in the hippocampus area of rats and the AChE activity in the frontal cortex area of rats in the animal model of β-amyloid-induced learning impairment.

FIGS. 12A and 12B show that compared to rats in the Sham group, the AChE activity in the hippocampus area and frontal cortex area of the control group of rats given β-amyloid peptide 1-40 is significantly greater increase. However, the experimental group shows that Sample 15B can ameliorate the increase in AChE activity in the hippocampus area and frontal cortex area of rats that caused by β-amyloid peptide 1-40.

Example 11: Determination of the Content of Ganoderic Acid A in the Four-Ingredient Compound A. Methods
Ganoderic Acid a Content Determination:
1. Preparation of Reference Standard Stock Solution:
   Accurately weighed 10 mg of a reference standard of ganoderic acid A was placed in a 10 mL volumetric flask, and then methanol solution was added thereto, sonication was performed to completely dissolve the ganoderic acid A, and then the above solution was quantified to 10 mL to make the solution contains 1 mg ganoderic acid A per 1 mL to obtain a reference standard solution (1 mg/mL).
2. Repeatability of Injection:
   1 mL of the reference standard solution (1 mg/mL) was taken and placed it in a 10 mL volumetric flask, and then quantify to the graduated mark with methanol. The above solution (0.1 mg/mL) was injected five times through HPLC analysis (Repeatability of injection), and the relative standard deviation (RSD) of the calculated peak area of ganoderic acid A should not be greater than 2.0%.
3. Preparation of Calibration Curve (Ganoderic Acid a Standard):
   The stock solution of the reference standard was taken and diluted with methanol, and based on the sample concentration, ganoderic acid A standard was prepared for five concentrations, the concentration range thereof had to include 80-120% of the ganoderic acid A concentration in the sample, and the ganoderic acid A standard solutions with five concentrations were injected into high performance liquid chromatography (HPLC) for analysis, and the peak area was linearly regressed against the concentration, wherein R2 thereof should not be less than 0.995.
4. Test Article Preparation:
   1.0 g of the test article (*Ganoderma* extract (Sample 1) or Sample 15B) was placed in a 20 mL volumetric flask, then about 10 mL of pure water added thereto, and the volumetric flask was placed in a water bath for sonication 10 minutes. After standing to cool, pure water was added to the volumetric flask to quantify to 20 mL to form an inspection sample solution. An appropriate amount of the inspection sample solution was centrifuged (10000 rpm, 5 minutes) and filtered with a 0.45 μm filter membrane, and then high performance liquid chromatography analysis was performed to calculate the content of ganoderic acid A in the test article.
5. High Performance Liquid Chromatography Analysis Conditions:
   Chromatography column type: Inertsil 5 ODS-2 4.6×250 mm or equivalent
   Detection wavelength: 257 nm
   Pump flow rate: 1.0 mL/minute
   Analysis time per sample: 120 minutes
   Total injection volume: 20 μL
   Mobile phase preparation:
   Mobile phase A=10% MeOH in $CH_3CN$ (volume ratio)
   Mobile phase B=0.075% phosphoric acid aqueous solution (522 μL of 85% phosphoric acid (density=1.685 g/mL) was placed in a 1 L volumetric flask, and diluted with pure water to the graduated mark).
6. Calculation of Ganoderic Acid a Content
   The content of ganoderic acid A (mg/g)=the concentration of ganoderic acid A in the inspection sample (mg/mL)×20 (mL)

B. Results
The inspection samples for the ganoderic acid A standard, the *Ganoderma* extract (Sample 1) and Sample 15B prepared as described above were subjected to the above-mentioned high performance liquid chromatography analysis and the content of ganoderic acid A in the Sample 15B was calculated. The results are shown in FIG. 13.

Figure 13:
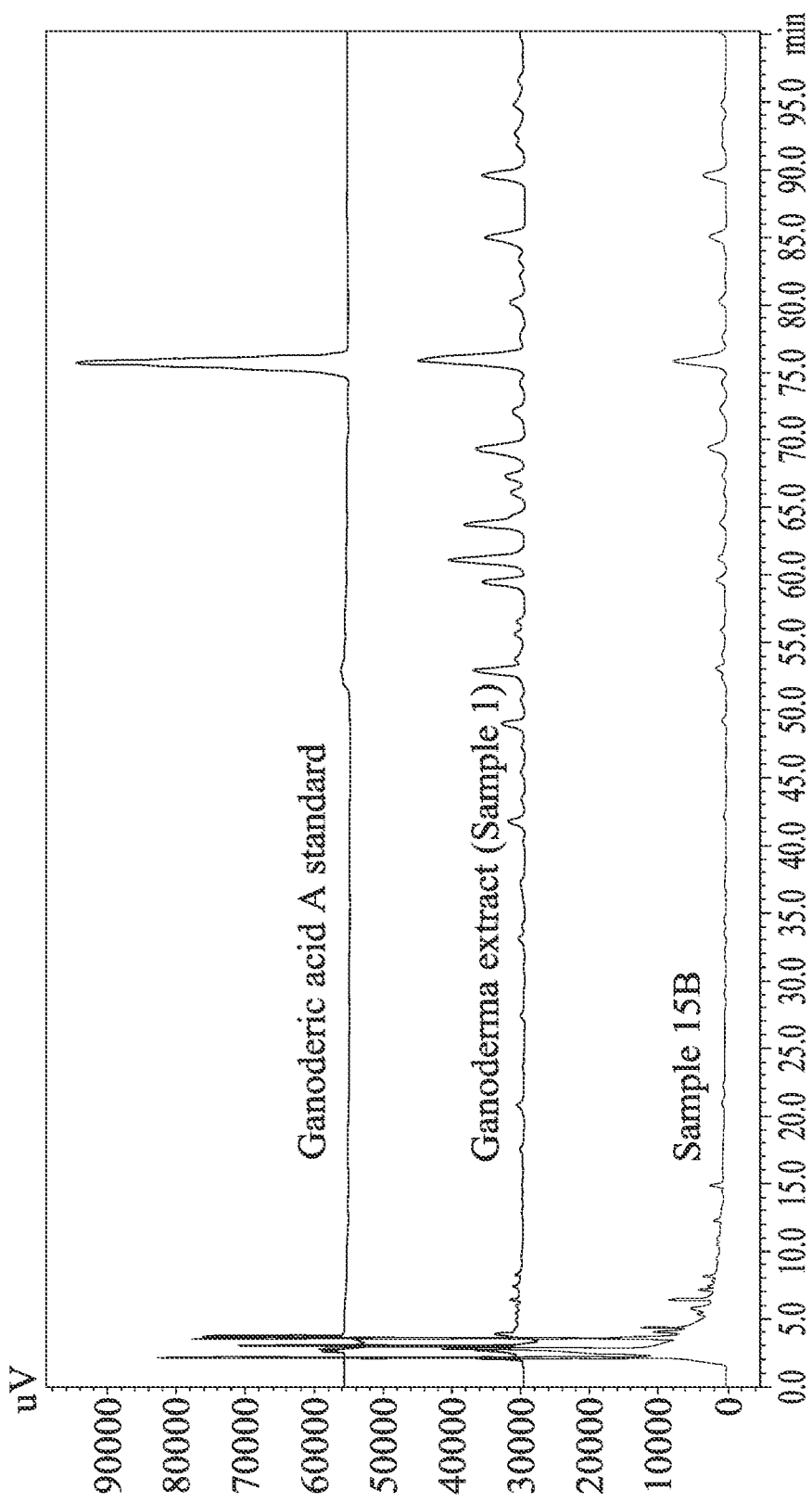
FIG. 13 shows the results of high performance liquid chromatography (HPLC) analysis of Sample 15B.

Referring to FIG. 13, based on the calibration curve of the above-mentioned standard, the content of ganoderic acid A in the *Ganoderma* extract and Sample 15B can be calculated to be 66.3 mg/g and 4.96 mg/g, respectively.

By determining the content of ganoderic acid A in the sample, the quality of the sample can be confirmed.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A composition for inhibiting intestinal permeability, treating leaky gut related diseases and/or preventing leaky gut related diseases, comprising:
a herbal compound material or a herbal compound extract,
wherein the herbal compound material consists of:
Ganoderma;
red jujube;
longan; and
lotus seed,
wherein in the herbal compound material, a weight ratio of Ganoderma, red jujube, longan and lotus seed is 0.1-15:0.6-2:0.6-2:0.6-5, and
wherein the herbal compound extract consists of:
Ganoderma extract;
red jujube extract;
longan extract; and
lotus seed extract,
wherein a weight ratio of Ganoderma, red jujube, longan and lotus seed as preparation raw materials which are respectively needed to obtain the Ganoderma extract, the red jujube extract, the longan extract and the lotus seed extract contained in the herbal compound extract is 0.1-15:0.6-2:0.6-2:0.6-5, and
wherein the herbal compound material or herbal compound extract is capable of inhibiting intestinal permeability, treating leaky gut related diseases and/or preventing leaky gut related diseases,
wherein the leaky gut related diseases comprise inflammatory bowel disease, celiac disease, irritable bowel syndrome, acute pancreatitis, non-alcoholic steatohepatitis, alcoholic cirrhosis, type 1 diabetes, type 2 diabetes, obesity, chronic kidney disease, cardiovascular disease, multiple organ failure syndrome, AIDS, asthma, eczema, psoriasis, autism, depression, anxiety, schizophrenia, bipolar disorder, Alzheimer's disease, Parkinson's disease, multiple sclerosis, amyotrophic lateral sclerosis, ankylosing spondylitis, fibromyalgia, chronic sleep fragmentation or insomnia.

2. The composition for inhibiting intestinal permeability, treating leaky gut related diseases and/or preventing leaky gut related diseases as claimed in claim 1, wherein the Ganoderma comprises Ganoderma lingzhi, Ganoderma sinensis or Ganoderma lucidum.

3. The composition for inhibiting intestinal permeability, treating leaky gut related diseases and/or preventing leaky gut related diseases as claimed in claim 1, wherein the red jujube comprises grey jujube, jixin jujube, winter jujube, big jujube, small jujube or golden silk jujube.

4. The composition for inhibiting intestinal permeability, treating leaky gut related diseases and/or preventing leaky gut related diseases as claimed in claim 1, wherein the longan comprises Fen Ke longan, Hong Ke longan or Qing Ke longan.

5. The composition for inhibiting intestinal permeability, treating leaky gut related diseases and/or preventing leaky gut related diseases as claimed in claim 1, wherein the lotus seed comprises red lotus seed or white lotus seed.

6. The composition for inhibiting intestinal permeability, treating leaky gut related diseases and/or preventing leaky gut related diseases as claimed in claim 1, wherein in the composition for modulating intestinal permeability and/or treating and/or preventing leaky gut related disease, the composition per gram contains 0.2-20 mg of ganoderic acid A.

7. The composition for inhibiting intestinal permeability, treating leaky gut related diseases and/or preventing leaky gut related diseases as claimed in claim 1, wherein, in the herbal compound material, a weight ratio of Ganoderma, red jujube, longan and lotus seed is 1:1:1:1.

8. The composition for inhibiting intestinal permeability, treating leaky gut related diseases and/or preventing leaky gut related diseases as claimed in claim 1, wherein in the herbal compound material, a weight ratio of Ganoderma, red jujube, longan and lotus seed is 3:1:1:1.

9. The composition for inhibiting intestinal permeability, treating leaky gut related diseases and/or preventing leaky gut related diseases as claimed in claim 1, wherein a weight ratio of Ganoderma, red jujube, longan and lotus seed as preparation raw materials which are respectively needed to obtain the Ganoderma extract, the red jujube extract, the longan extract and the lotus seed extract contained in the herbal compound extract is 1:1:1:1.

10. The composition for inhibiting intestinal permeability, treating leaky gut related diseases and/or preventing leaky gut related diseases as claimed in claim 1, wherein a weight ratio of Ganoderma, red jujube, longan and lotus seed as preparation raw materials which are respectively needed to obtain the Ganoderma extract, the red jujube extract, the longan extract and the lotus seed extract contained in the herbal compound extract is 3:1:1:1.

11. The composition for inhibiting intestinal permeability, treating leaky gut related diseases and/or preventing leaky gut related diseases as claimed in claim 1, further comprising a pharmaceutically acceptable carrier or salt.

12. The composition for inhibiting intestinal permeability, treating leaky gut related diseases and/or preventing leaky gut related diseases as claimed in claim 11, wherein in the composition for inhibiting intestinal permeability, treating leaky gut related diseases and/or preventing leaky gut related diseases, a content of the herbal compound material or a herbal compound extract is 10-99.5 wt %.

13. The composition for inhibiting intestinal permeability, treating leaky gut related diseases and/or preventing leaky gut related diseases as claimed in claim 1, wherein the composition for inhibiting intestinal permeability, treating leaky gut related diseases and/or preventing leaky gut related diseases is a pharmaceutical composition or a health care composition.

14. The composition for inhibiting intestinal permeability, treating leaky gut related diseases and/or preventing leaky gut related diseases as claimed in claim 13, wherein the oral form of the pharmaceutical composition or health care composition comprises tablets, granules, powders, pellet in capsules, capsules, coated tablets, solutions or instant powders.

* * * * *